US012017041B2

(12) United States Patent
Nakagawa et al.

(10) Patent No.: US 12,017,041 B2
(45) Date of Patent: Jun. 25, 2024

(54) PRIMING METHOD FOR INFUSION SET, AND INFUSION SET

(71) Applicants: JMS CO., LTD., Hiroshima (JP); Kyoto University, Kyoto (JP)

(72) Inventors: Hirofumi Nakagawa, Hiroshima (JP); Tadashi Okiyama, Hiroshima (JP); Masashi Kanai, Kyoto (JP); Yoko Hamabe, Kyoto (JP)

(73) Assignees: JMS Co., Ltd., Hiroshima (JP); Kyoto University, Kyoto (JP)

( * ) Notice: Subject to any disclaimer, the term of this patent is extended or adjusted under 35 U.S.C. 154(b) by 923 days.

(21) Appl. No.: 17/048,309

(22) PCT Filed: Apr. 4, 2019

(86) PCT No.: PCT/JP2019/015026
§ 371 (c)(1),
(2) Date: Oct. 16, 2020

(87) PCT Pub. No.: WO2019/203014
PCT Pub. Date: Oct. 24, 2019

(65) Prior Publication Data
US 2021/0162124 A1  Jun. 3, 2021

(30) Foreign Application Priority Data

Apr. 17, 2018 (JP) ................................ 2018-079106

(51) Int. Cl.
*A61M 5/168* (2006.01)
*A61M 5/14* (2006.01)
(Continued)

(52) U.S. Cl.
CPC ...... *A61M 5/16813* (2013.01); *A61M 5/1408* (2013.01); *A61M 5/1411* (2013.01);
(Continued)

(58) Field of Classification Search
CPC ............ A61M 5/16813; A61M 5/1408; A61M 5/1411; A61M 39/10; A61M 39/22; A61M 2005/1402
See application file for complete search history.

(56) References Cited

U.S. PATENT DOCUMENTS

2003/0004463 A1   1/2003  Reilly et al.
2011/0132482 A1*  6/2011  Honma ............... A61M 39/223
                                           285/133.11
(Continued)

FOREIGN PATENT DOCUMENTS

JP  2013-525065   6/2013
JP  2013-252165  12/2013
(Continued)

OTHER PUBLICATIONS

Extended European Search Report issued in corresponding European Patent Application No. 19789232.6, dated Mar. 22, 2022, 8 pages.

*Primary Examiner* — James D Ponton
(74) *Attorney, Agent, or Firm* — HSML P.C.

(57) ABSTRACT

A first open/close valve (12a), a drip chamber (14), and a variable valve (17) are provided in this order on a first flow path (10a) from a first connector (11a) side toward a downstream connector (19) side. A second flow path (10b), on which a second open/close valve (12b) is provided, is connected to a section of the first flow path between the first open/close valve and the drip chamber. A priming method includes a first step of causing the first liquid to flow from a first container (20a) into the first flow path and priming the first flow path using the first liquid, and a second step of causing the second liquid to flow from a second container (20b) into the second flow path and priming the second flow path using the second liquid. In the second step, the second (Continued)

liquid moves air that has been present in the second flow path toward the first container (20*a*).

24 Claims, 7 Drawing Sheets

(51) Int. Cl.
*A61M 39/10* (2006.01)
*A61M 39/22* (2006.01)

(52) U.S. Cl.
CPC ............ *A61M 39/10* (2013.01); *A61M 39/22* (2013.01); *A61M 2005/1402* (2013.01)

(56) References Cited

U.S. PATENT DOCUMENTS

| | | |
|---|---|---|
| 2011/0276010 A1 | 11/2011 | Davis et al. |
| 2015/0247597 A1 | 9/2015 | Okiyama |
| 2015/0265499 A1 | 9/2015 | Takeuchi |
| 2015/0297830 A1* | 10/2015 | Okiyama .............. A61M 39/28 604/246 |
| 2018/0021511 A1 | 1/2018 | Fukuoka et al. |
| 2018/0021512 A1 | 1/2018 | Fukuoka et al. |
| 2018/0064923 A1 | 3/2018 | Takeuchi |
| 2019/0143023 A1* | 5/2019 | Yuds .................. B01D 19/0073 604/4.01 |
| 2019/0247576 A1 | 8/2019 | Okiyama et al. |

FOREIGN PATENT DOCUMENTS

| | | |
|---|---|---|
| JP | 2014-030489 | 2/2014 |
| JP | 2014-079355 | 5/2014 |
| JP | 5774802 B | 9/2015 |
| KR | 10-2017-0106498 | 9/2017 |
| WO | 2010/001939 | 1/2010 |
| WO | 2013/154050 | 10/2013 |
| WO | 2016/133139 | 8/2016 |
| WO | 2017/006637 | 1/2017 |
| WO | 2018/074294 | 4/2018 |

* cited by examiner

PRIMING METHOD FOR INFUSION SET, AND INFUSION SET

TECHNICAL FIELD

The present invention relates to a method for priming an infusion set that is to be used to administer a liquid such as a medical solution via a patient's vein. Also, the present invention relates to this infusion set.

BACKGROUND ART

In the medical field, infusion to administer medicines, nutrients, electrolytes, or the like via a patient's vein is widely performed. For example, in the case of administering an anti-cancer agent, it is necessary to sequentially administer, to a patient, not only a medical solution that contains the anti-cancer agent but also a plurality of liquids, such as a premedication and a physiological saline for washing out flow paths. The plurality of liquids are stored separately in a plurality of respective infusion bags. An infusion set that includes a main line and at least one sub-injection line is used to bring a plurality of infusion bags into communication with a needle that has been inserted into a patient's vein.

Before infusion is started, an operation, which is called priming, to replace air that is within a flow path in the infusion set with a priming solution needs to be performed. Patent Document 1 describes a priming method in which a priming solution (physiological saline) in an infusion bag is introduced into an entire infusion set that includes a main line and a side-injection line, with the infusion bag in which the priming solution is stored connected to the main line, and with an infusion set not connected to the side-injection line.

PRIOR ART DOCUMENTS

Patent Document

[Patent Document 1] JP 5774802B
[Patent Document 2] WO 2013/154050
[Patent Document 3] JP 2014-079355A
[Patent Document 4] JP 2013-252165A
[Patent Document 5] WO 2016/133139

DISCLOSURE OF INVENTION

Problem to be Solved by the Invention

In the above priming method, the same priming solution is introduced into both the main line and the side-injection line. It is desired, in some cases, that the lines are primed using liquids stored in infusion bags that are connected to the respective lines.

Meanwhile, when priming is performed using a medical solution (hazardous medical solution) that contains a hazardous medicine such as an anti-cancer agent, leakage of this hazardous medical solution or air that has come into contact therewith to the outside needs to be avoided since it may expose an operator to the medicine.

An object of the present invention is to enable an operator to prime an infusion set that includes a main line and a side-injection line without being exposed to a medicine.

Means for Solving Problem

A first infusion set of the present invention includes: a first flow path having, at one end, a first connector, which is to be connected to a first container for storing a first liquid, and having a downstream connector at another end; a first open/close valve, a drip chamber, and a variable valve that are provided in this order on the first flow path from the first connector side toward the downstream connector side; a second flow path having, at one end, a second connector, which is to be connected to a second container for storing a second liquid, another end of the second flow path being connected to a section of the first flow path between the first open/close valve and the drip chamber; and a second open/close valve provided on the second flow path.

A first priming method of the present invention for priming the first infusion set includes: a first priming step of causing the first liquid to flow from the first container into the first flow path and priming the first flow path using the first liquid; and a second priming step of causing the second liquid to flow from the second container into the second flow path and priming the second flow path using the second liquid. In the second priming step, the second liquid moves air that has been present in the second flow path toward the first container.

A second infusion set of the present invention includes: a first flow path having, at one end, a first connector, which is to be connected to a first container for storing a first liquid, and having a downstream connector at another end; a first open/close valve, a drip chamber, and a variable valve that are provided in this order on the first flow path from the first connector side toward the downstream connector side; a second flow path having, at one end, a second connector, which is to be connected to a second container for storing a second liquid, another end of the second flow path being connected to a section of the first flow path between the first open/close valve and the drip chamber; a second open/close valve provided on the second flow path; a collection flow path with one end connected to the section of the first flow path, the collection flow path having, at another end, a collection container connector, which is to be connected to a collection container; and a collection flow path open/close valve provided on the collection flow path.

A second priming method of the present invention for priming the second infusion set includes: a first priming step of causing the first liquid to flow from the first container into the first flow path and priming the first flow path using the first liquid; and a second priming step of causing the second liquid to flow from the second container into the second flow path and priming the second flow path using the second liquid. In the second priming step, the second liquid moves air that has been present in the second flow path toward the collection container.

A third infusion set of the present invention includes: a first flow path having, at one end, a first connector, which is to be connected to a first container for storing a first liquid, and having a downstream connector at another end; a first open/close valve, a drip chamber, and a variable valve that are provided in this order on the first flow path from the first connector side toward the downstream connector side; a second flow path having, at one end, a second connector, which is to be connected to a second container for storing a second liquid, another end of the second flow path being connected to a section of the first flow path between the first open/close valve and the drip chamber; a second open/close valve provided on the second flow path; a collection flow path with one end in communication with a gas storing portion in the drip chamber, the collection flow path having, at another end, a collection container connector, which is to be connected to a collection container; and a collection flow path open/close valve provided on the collection flow path.

A third priming method of the present invention for priming the third infusion set includes: a first priming step of causing the first liquid to flow from the first container into the first flow path and priming the first flow path using the first liquid; and a second priming step of causing the second liquid to flow from the second container into the second flow path and priming the second flow path using the second liquid. In the second priming step, the second liquid moves air that has been present in the second flow path toward the collection container through the gas storing portion in the drip chamber and the collection flow path.

A fourth infusion set of the present invention includes: a first flow path having, at one end, a first connector, which is to be connected to a first container for storing a first liquid, and having a downstream connector at another end; a first open/close valve, a drip chamber, and a variable valve that are provided in this order on the first flow path from the first connector side toward the downstream connector side; a second flow path having, at one end, a second connector, which is to be connected to a second container for storing a second liquid, another end of the second flow path being connected to a section of the first flow path between the first open/close valve and the drip chamber; a second open/close valve provided on the second flow path; a bypass flow path with one end in communication with a gas storing portion in the drip chamber, and another end in communication with a portion of the first flow path on the first connector side of the first open/close valve, or with the first connector; a bypass flow path open/close valve provided on the bypass flow path; a collection flow path with one end connected to the section of the first flow path, the collection flow path having, at another end, a collection container connector, which is to be connected to a collection container; and a collection flow path open/close valve provided on the collection flow path.

A fourth priming method of the present invention for priming the fourth infusion set includes: a first priming step of causing the first liquid to flow from the first container into the first flow path and priming the first flow path using the first liquid; and a second priming step of causing the second liquid to flow from the second container into the second flow path and priming the second flow path using the second liquid. The second priming step includes: a first part of the second priming step of moving, using the second liquid, air that has been present in the second flow path toward the collection container through the collection flow path, and a second part of the second priming step of moving, using the second liquid, air that is present forward of the second liquid in a direction in which the second liquid flows, toward the first container through the gas storing portion in the drip chamber and the bypass flow path.

A fifth infusion set of the present invention includes: a first flow path having, at one end, a first connector, which is to be connected to a first container for storing a first liquid, and having a downstream connector at another end; a first open/close valve, a drip chamber, and a variable valve that are provided in this order on the first flow path from the first connector side toward the downstream connector side; a second flow path having, at one end, a second connector, which is to be connected to a second container for storing a second liquid, another end of the second flow path being connected to a section of the first flow path between the first open/close valve and the drip chamber; a second open/close valve provided on the second flow path; a bypass flow path with one end in communication with a gas storing portion in the drip chamber, and another end in communication with a portion of the first flow path on the first connector side of the first open/close valve, or with the first connector; a bypass flow path open/close valve provided on the bypass flow path; a collection flow path with one end connected to a portion of the bypass flow path between the drip chamber and the bypass flow path open/close valve, the collection flow path having, at another end, a collection container connector, which is to be connected to a collection container; and a collection flow path open/close valve provided on the collection flow path.

A fifth priming method of the present invention for priming the fifth infusion set includes: a first priming step of causing the first liquid to flow from the first container into the first flow path and priming the first flow path using the first liquid; and a second priming step of causing the second liquid to flow from the second container into the second flow path and priming the second flow path using the second liquid. In the second priming step, the second liquid moves air that has been present in the second flow path toward the collection container through the gas storing portion in the drip chamber, the bypass flow path, and the collection flow path, or toward the first container through the gas storing portion in the drip chamber and the bypass flow path.

Effects of the Invention

According to the present invention, the first priming step of priming the first flow path using the first liquid is performed, and thereafter, the second priming step of priming the second flow path using the second liquid is performed. The first and second flow paths can be primed using the first and second liquids that are stored in the first and second container that are connected to the first and second flow paths, respectively.

In the second priming step, the second liquid moves air that has been present in the second flow path toward a predetermined container. In the case where the second liquid is a hazardous medical solution, it is unlikely that the second liquid or air that has come into contact therewith leaks out to the outside. For this reason, an operator can perform priming without being exposed to the medical solution.

DESCRIPTION OF THE INVENTION

Figure 1:
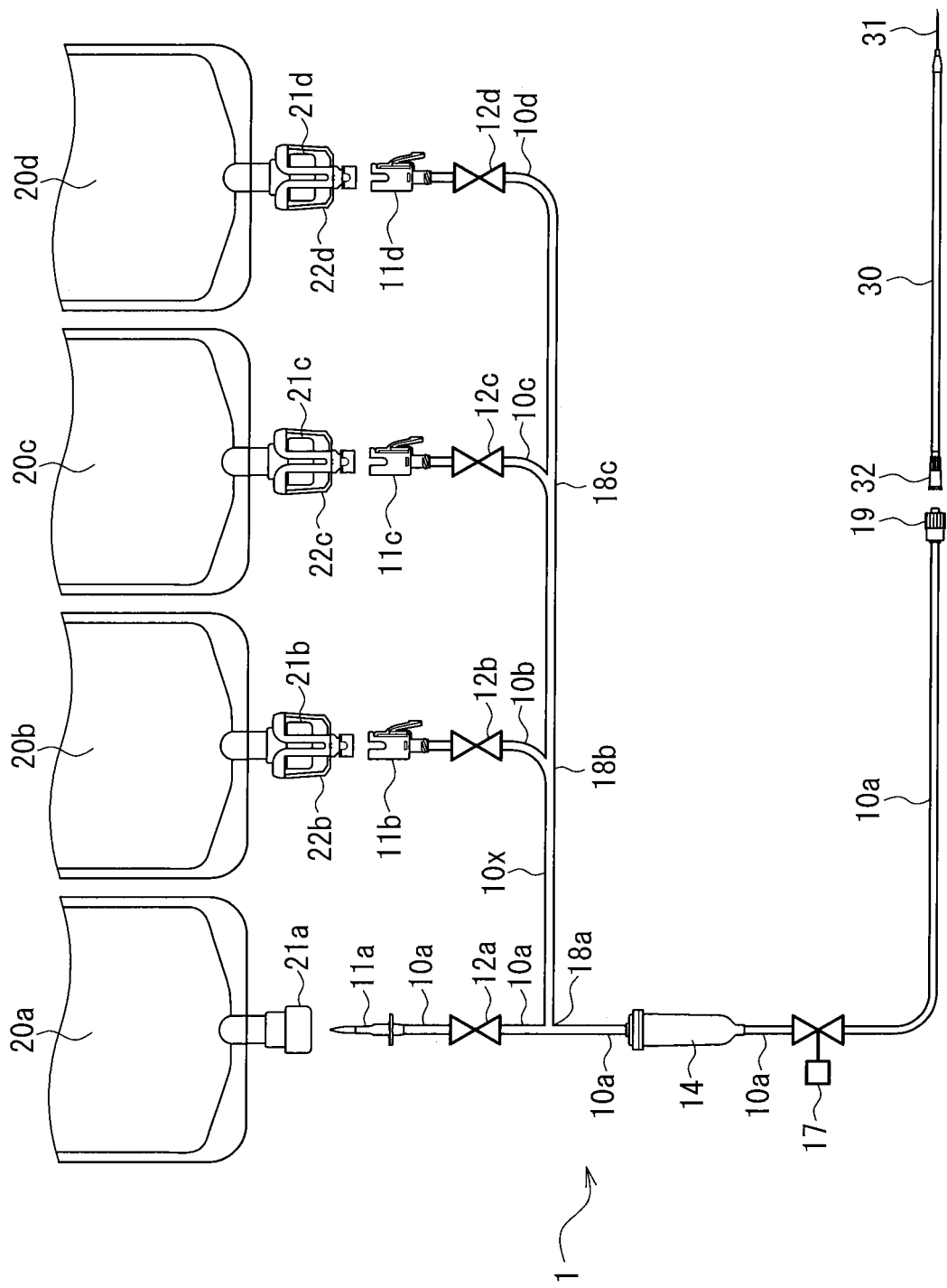
FIG. 1 shows an infusion set according to Embodiment 1 of the present invention.

A first infusion set of the present invention includes: a first flow path having, at one end, a first connector, which is to be connected to a first container for storing a first liquid, and having a downstream connector at another end; a first open/close valve, a drip chamber, and a variable valve that are provided in this order on the first flow path from the first connector side toward the downstream connector side; a second flow path having, at one end, a second connector, which is to be connected to a second container for storing a second liquid, another end of the second flow path being connected to a section of the first flow path between the first open/close valve and the drip chamber; and a second open/close valve provided on the second flow path.

A first priming method of the present invention for priming the first infusion set includes: a first priming step of causing the first liquid to flow from the first container into the first flow path and priming the first flow path using the first liquid; and a second priming step of causing the second liquid to flow from the second container into the second flow path and priming the second flow path using the second liquid. In the second priming step, the second liquid moves air that has been present in the second flow path toward the first container.

In the first priming step of the first priming method, the second open/close valve may be closed and the first open/close valve and the variable valve may be opened to cause the first liquid to flow from the first container toward the downstream connector. This is advantageous for priming the entire first flow path from the first connector to the downstream connector using the first liquid in a simply manner.

In the first priming method, after the first priming step, in a state where the first liquid is being caused to flow from the first container toward the downstream connector with the second open/close valve closed and with the first open/close valve and the variable valve opened, the variable valve may be closed and the second open/close valve may be opened to start the second priming step. Thus, drip injection of the first liquid can be readily switched to priming of the second flow path.

Preferably, the variable valve is closed when an interface between the first liquid and air that has flowed out, following the first liquid, from the first container reaches the section of the first flow path in a state where the first liquid is being caused to flow from the first container toward the downstream connector. This mode is advantageous for reducing the likelihood that air mixes between the first liquid and the second liquid in the case where the whole quantity of the first liquid in the first container is administered to a patient, and subsequently the second liquid is sequentially administered to the patient.

The first infusion set may further include: a third flow path having, at one end, a third connector, which is to be connected to a third container for storing a third liquid, another end of the third flow path being connected to the section of the first flow path; and a third open/close valve provided on the third flow path. The first priming method may further include a third priming step of causing the third liquid to flow from the third container into the third flow path and priming the third flow path using the third liquid. In the third priming step, the third liquid may move air that has been present in the third flow path toward the first container. Thus, the third flow path can be primed using the third liquid stored in the third container that is connected to the third flow path. In the case where the third liquid is a hazardous medical solution, it is unlikely that the third liquid or air that has come into contact therewith leaks out to the outside. For this reason, the operator can prime the third flow path using the third liquid without being exposed to the medicine.

In the third priming step of the first priming method, the third liquid may move, toward the first container, air that has flowed out of the second container following the second liquid. This mode reduces the likelihood that, in the case where the second liquid is a hazardous medical solution, air that has come into contact with the second liquid leaks out to the outside.

In the first priming method, after the second priming step, when an interface between the second liquid and air that has flowed out, following the second liquid, from the second container reaches the section of the first flow path in a state where the second liquid is being caused to flow from the second container toward the downstream connector with the first open/close valve and the third open/close valve closed and with the second open/close valve and the variable valve opened, the second open/close valve and the variable valve may be closed and the third open/close valve and the first open/close valve may opened to start the third priming step. This mode is advantageous for reducing the likelihood that air mixes between the second liquid and the third liquid in the case where the whole quantity of the second liquid in the second container is administered to the patient, and subsequently the third liquid is sequentially administered to the patient.

The first infusion set may further include: a bypass flow path with one end in communication with a gas storing portion in the drip chamber, and another end in communication with a portion of the first flow path on the first connector side of the first open/close valve, or with the first connector; and a bypass flow path open/close valve provided on the bypass flow path. In the second priming step, the second liquid may move air that has been present in the second flow path toward the first container through the gas storing portion in the drip chamber and the bypass flow path. According to this mode, the second liquid and air that has been present in the second flow path can be reliably separated from each other using the drip chamber.

In the first priming step of the first priming method, the second open/close valve and the bypass flow path open/close valve may be closed and the first open/close valve and the variable valve may be opened to cause the first liquid to flow from the first container toward the downstream connector. This is advantageous for priming the entire first flow path from the first connector to the downstream connector using the first liquid in a simply manner.

In the first priming method, after the first priming step, in a state where the first liquid is being caused to flow from the first container toward the downstream connector with the second open/close valve and the bypass flow path open/close valve closed and with the first open/close valve and the variable valve opened, the first open/close valve and the variable valve may be closed and the second open/close valve and the bypass flow path open/close valve may be opened to start the second priming step. Thus, drip injection of the first liquid can be readily switched to priming of the second flow path.

Preferably, the first open/close valve and the variable valve are closed when an interface between the first liquid and air that has flowed out, following the first liquid, from the first container reaches the section of the first flow path or when dripping of the first liquid in the drip chamber ends in a state where the first liquid is being caused to flow from the first container toward the downstream connector. This mode is advantageous for reducing the likelihood that air mixes between the first liquid and the second liquid in the case where the whole quantity of the first liquid in the first container is administered to a patient, and subsequently the second liquid is sequentially administered to the patient.

The first infusion set may further include: a third flow path having, at one end, a third connector, which is to be connected to a third container for storing a third liquid, another end of the third flow path being connected to the section of the first flow path; and a third open/close valve provided on the third flow path. The first priming method may further include a third priming step of causing the third liquid to flow from the third container into the third flow path and priming the third flow path using the third liquid. In the third priming step, the third liquid may move air that has been present in the third flow path toward the first container through the gas storing portion in the drip chamber and the bypass flow path. In the case where the third liquid is a hazardous medical solution, it is unlikely that the third liquid or air that has come into contact therewith leaks out to the outside. For this reason, the operator can prime the third flow path using the third liquid without being exposed to the medicine.

In the third priming step of the first priming method, the third liquid may move air that has flowed out of the second container following the second liquid, toward the first container through the gas storing portion in the drip chamber and the bypass flow path. This mode reduces the likelihood that, in the case where the second liquid is a hazardous medical solution, air that has come into contact with the second liquid leaks out to the outside.

After the second priming step, when an interface between the second liquid and air that has flowed out, following the second liquid, from the second container reaches the section of the first flow path, or when dripping of the second liquid in the drip chamber ends, in a state where the second liquid is being caused to flow from the second container toward the downstream connector with the first open/close valve, the third open/close valve, and the bypass flow path open/close valve closed and with the second open/close valve and the variable valve opened, the second open/close valve and the variable valve may be closed and the third open/close valve and the bypass flow path open/close valve may be opened to start the third priming step. This mode is advantageous for reducing the likelihood that air mixes between the second liquid and the third liquid in the case where the whole quantity of the second liquid in the second container is administered to a patient, and subsequently the third liquid is sequentially administered to the patient.

A second infusion set of the present invention includes: a first flow path having, at one end, a first connector, which is to be connected to a first container for storing a first liquid, and having a downstream connector at another end; a first open/close valve, a drip chamber, and a variable valve that are provided in this order on the first flow path from the first connector side toward the downstream connector side; a second flow path having, at one end, a second connector, which is to be connected to a second container for storing a second liquid, another end of the second flow path being connected to a section of the first flow path between the first open/close valve and the drip chamber; a second open/close valve provided on the second flow path; a collection flow path with one end connected to the section of the first flow path, the collection flow path having, at another end, a collection container connector, which is to be connected to a collection container; and a collection flow path open/close valve provided on the collection flow path.

A second priming method of the present invention for priming the second infusion set includes: a first priming step of causing the first liquid to flow from the first container into the first flow path and priming the first flow path using the first liquid; and a second priming step of causing the second liquid to flow from the second container into the second flow path and priming the second flow path using the second liquid. In the second priming step, the second liquid moves air that has been present in the second flow path toward the collection container.

In the first priming step of the second priming method, the second open/close valve and the collection flow path open/close valve may be closed and the first open/close valve and the variable valve may be opened to cause the first liquid to flow from the first container toward the downstream connector. This is advantageous for priming the entire first flow path from the first connector to the downstream connector using the first liquid in a simply manner.

In the second priming method, after the first priming step, in a state where the first liquid is being caused to flow from the first container toward the downstream connector with the second open/close valve and the collection flow path open/close valve closed and with the first open/close valve and the variable valve opened, the first open/close valve and the variable valve may be closed and the second open/close valve and the collection flow path open/close valve may be opened to start the second priming step. Thus, drip injection of the first liquid can be readily switched to priming of the second flow path.

Preferably, the first open/close valve and the variable valve are closed when an interface between the first liquid and air that has flowed out, following the first liquid, from the first container reaches the section of the first flow path in a state where the first liquid is being caused to flow from the first container toward the downstream connector. This mode is advantageous for reducing the likelihood that air mixes between the first liquid and the second liquid in the case where the whole quantity of the first liquid in the first container is administered to a patient, and subsequently the second liquid is sequentially administered to the patient.

The second infusion set may further include: a third flow path having, at one end, a third connector, which is to be connected to a third container for storing a third liquid, another end of the third flow path being connected to the section of the first flow path; and a third open/close valve provided on the third flow path. The second priming method may further include a third priming step of causing the third liquid to flow from the third container into the third flow path and priming the third flow path using the third liquid. In the third priming step, the third liquid may move air that has been present in the third flow path toward the collection container through the collection flow path. Thus, the third flow path can be primed using the third liquid stored in the third container that is connected to the third flow path. In the case where the third liquid is a hazardous medical solution, it is unlikely that the third liquid or air that has come into contact therewith leaks out to the outside. For this reason, the operator can prime the third flow path using the third liquid without being exposed to the medicine.

In the third priming step of the second priming method, the third liquid may move air that has flowed out of the second container following the second liquid, toward the collection container through the collection flow path. This mode reduces the likelihood that air that has come into contact with the second liquid leaks out to the outside in the case where the second liquid is a hazardous medical solution.

In the second priming method, after the second priming step, when an interface between the second liquid and air that has flowed out, following the second liquid, from the second container reaches the section of the first flow path in a state where the second liquid is being caused to flow from the second container toward the downstream connector with the first open/close valve, the third open/close valve, and the collection flow path open/close valve closed and with the second open/close valve and the variable valve opened, the second open/close valve and the variable valve may be closed and the third open/close valve and the collection flow path open/close valve may be opened to start the third priming step. This mode is advantageous for reducing the likelihood that air mixes between the second liquid and the third liquid when the whole quantity of the second liquid in the second container is administered to a patient, and subsequently the third liquid is sequentially administered to the patient.

A third infusion set of the present invention includes: a first flow path having, at one end, a first connector, which is to be connected to a first container for storing a first liquid, and having a downstream connector at another end; a first open/close valve, a drip chamber, and a variable valve that are provided in this order on the first flow path from the first connector side toward the downstream connector side; a second flow path having, at one end, a second connector, which is to be connected to a second container for storing a second liquid, another end of the second flow path being connected to a section of the first flow path between the first open/close valve and the drip chamber; a second open/close valve provided on the second flow path; a collection flow path with one end in communication with a gas storing portion in the drip chamber, the collection flow path having, at another end, a collection container connector, which is to be connected to a collection container; and a collection flow path open/close valve provided on the collection flow path.

A third priming method of the present invention for priming the third infusion set includes: a first priming step of causing the first liquid to flow from the first container into the first flow path and priming the first flow path using the first liquid; and a second priming step of causing the second liquid to flow from the second container into the second flow path and priming the second flow path using the second liquid. In the second priming step, the second liquid moves air that has been present in the second flow path toward the collection container through the gas storing portion in the drip chamber and the collection flow path.

In the first priming step of the third priming method, the second open/close valve and the collection flow path open/close valve may be closed and the first open/close valve and the variable valve may be opened to cause the first liquid to flow from the first container toward the downstream connector. This is advantageous for priming the entire first flow path from the first connector to the downstream connector using the first liquid in a simply manner.

In the third priming method, after the first priming step, in a state where the first liquid is being caused to flow from the first container toward the downstream connector with the second open/close valve and the collection flow path open/close valve closed and with the first open/close valve and the variable valve opened, the first open/close valve and the variable valve may be closed and the second open/close valve and the collection flow path open/close valve may be opened to start the second priming step. Thus, drip injection of the first liquid can be readily switched to priming of the second flow path.

Preferably, the first open/close valve and the variable valve are closed when an interface between the first liquid and air that has flowed out, following the first liquid, from the first container reaches the section of the first flow path or when dripping of the first liquid in the drip chamber ends in a state where the first liquid is being caused to flow from the first container toward the downstream connector. This mode is advantageous for reducing the likelihood that air mixes between the first liquid and the second liquid in the case where the whole quantity of the first liquid in the first container is administered to a patient, and subsequently the second liquid is sequentially administered to the patient.

The third infusion set may further include: a third flow path having, at one end, a third connector, which is to be connected to a third container for storing a third liquid, another end of the third flow path being connected to the section of the first flow path; and a third open/close valve provided on the third flow path. The third priming method may further include a third priming step of causing the third liquid to flow from the third container into the third flow path and priming the third flow path using the third liquid. In the third priming step, the third liquid may move air that has been present in the third flow path toward the collection container through the gas storing portion in the drip chamber and the collection flow path. Thus, the third flow path can be primed using the third liquid stored in the third container that is connected to the third flow path. In the case where the third liquid is a hazardous medical solution, it is unlikely that the third liquid or air that has come into contact therewith leaks out to the outside. For this reason, the operator can prime the third flow path using the third liquid without being exposed to the medicine.

In the third priming step of the third priming method, the third liquid may move air that has flowed out of the second container following the second liquid, toward the collection container through the gas storing portion in the drip chamber and the collection flow path. This mode reduces the likelihood that air that has come into contact with the second liquid leaks out to the outside in the case where the second liquid is a hazardous medical solution.

In the third priming method, after the second priming step, when an interface between the second liquid and air that has flowed out, following the second liquid, from the second container reaches the section of the first flow path or when dripping of the second liquid in the drip chamber ends in a state where the second liquid is being caused to flow from the second container toward the downstream connector with the first open/close valve, the third open/close valve, and the collection flow path open/close valve closed and with the second open/close valve and the variable valve opened, the second open/close valve and the variable valve may be closed and the third open/close valve and the collection flow path open/close valve may be opened to start the third priming step. This mode is advantageous for reducing the likelihood that air mixes between the second liquid and the third liquid in the case where the whole quantity of the second liquid in the second container is administered to a patient, and subsequently the third liquid is sequentially administered to the patient.

A fourth infusion set of the present invention includes: a first flow path having, at one end, a first connector, which is to be connected to a first container for storing a first liquid, and having a downstream connector at another end; a first open/close valve, a drip chamber, and a variable valve that are provided in this order on the first flow path from the first connector side toward the downstream connector side; a second flow path having, at one end, a second connector, which is to be connected to a second container for storing a second liquid, another end of the second flow path being connected to a section of the first flow path between the first open/close valve and the drip chamber; a second open/close valve provided on the second flow path; a bypass flow path with one end in communication with a gas storing portion in the drip chamber, and another end in communication with a portion of the first flow path on the first connector side of the first open/close valve, or with the first connector; a bypass flow path open/close valve provided on the bypass flow path; a collection flow path with one end connected to the section of the first flow path, the collection flow path having, at another end, a collection container connector, which is to be connected to a collection container; and a collection flow path open/close valve provided on the collection flow path.

A fourth priming method of the present invention for priming the fourth infusion set includes: a first priming step of causing the first liquid to flow from the first container into the first flow path and priming the first flow path using the first liquid; and a second priming step of causing the second liquid to flow from the second container into the second flow path and priming the second flow path using the second liquid. The second priming step includes: a first part of the second priming step of moving, using the second liquid, air that has been present in the second flow path toward the collection container through the collection flow path; and a second part of the second priming step of moving, using the second liquid, air that is present forward of the second liquid in a direction in which the second liquid flows, toward the first container through the gas storing portion in the drip chamber and the bypass flow path.

In the first priming step of the fourth priming method, the second open/close valve, the bypass flow path open/close valve, and the collection flow path open/close valve may be closed and the first open/close valve and the variable valve may be opened to cause the first liquid to flow from the first container toward the downstream connector. This is advantageous for priming the entire first flow path from the first connector to the downstream connector using the first liquid in a simply manner.

In the fourth priming method, after the first priming step, in a state where the first liquid is being caused to flow from the first container toward the downstream connector with the second open/close valve, the bypass flow path open/close valve, and the collection flow path open/close valve closed and with the first open/close valve and the variable valve opened, the first open/close valve and the variable valve may be closed and the second open/close valve and the collection flow path open/close valve may be opened to start the first part of the second priming step and cause the second liquid to flow from the second container into the second flow path. After starting the first part of the second priming step, when the second liquid reaches the section of the first flow path, the collection flow path open/close valve may be closed and the bypass flow path open/close valve may be opened to start the second part of the second priming step and cause the second liquid to flow into the drip chamber. Thus, drip injection of the first liquid can be readily switched to priming of the second flow path.

Preferably, the first open/close valve and the variable valve are closed when an interface between the first liquid and air that has flowed out, following the first liquid, from the first container reaches the section of the first flow path or when dripping of the first liquid in the drip chamber ends in a state where the first liquid is being caused to flow from the first container toward the downstream connector. This mode is advantageous for reducing the likelihood that air mixes between the first liquid and the second liquid in the case where the whole quantity of the first liquid in the first container is administered to a patient, and subsequently the second liquid is sequentially administered to the patient.

The fourth infusion set may further include: a third flow path having, at one end, a third connector, which is to be connected to a third container for storing a third liquid, another end of the third flow path being connected to the section of the first flow path; and a third open/close valve provided on the third flow path. The fourth priming method may further include a third priming step of causing the third liquid to flow from the third container into the third flow path and priming the third flow path using the third liquid. The third priming step may include: a first part of the third priming step of moving, using the third liquid, air that has been present in the third flow path toward the collection container through the collection flow path; and a second part of the third priming step of moving, using the third liquid, air that is present forward of the third liquid in a direction in which the third liquid flows, toward the first container through the gas storing portion in the drip chamber and the bypass flow path. Thus, the third flow path can be primed using the third liquid stored in the third container that is connected to the third flow path. In the case where the third liquid is a hazardous medical solution, it is unlikely that the third liquid or air that has come into contact therewith leaks out to the outside. For this reason, the operator can prime the third flow path using the third liquid without being exposed to the medicine.

In the third priming step of the fourth priming method, the third liquid may move air that has flowed out of the second container following the second liquid, toward the collection container through the collection flow path, or toward the first container through the gas storing portion in the drip chamber and the bypass flow path. This mode reduces the likelihood that, in the case where the second liquid is a hazardous medical solution, air that has come into contact with the second liquid leaks out to the outside.

In the fourth priming method, after the second priming step, when an interface between the second liquid and air that has flowed out, following the second liquid, from the second container reaches the section of the first flow path, or when dripping of the second liquid in the drip chamber ends, in a state where the second liquid is being caused to flow from the second container toward the downstream connector with the first open/close valve, the third open/close valve, the bypass flow path open/close valve, and the collection flow path open/close valve closed and with the second open/close valve and the variable valve opened, the second open/close valve and the variable valve may be closed and the third open/close valve and the collection flow path open/close valve may be opened to start the first part of the third priming step and cause the third liquid to flow from the third container into the third flow path. After starting the first part of the third priming step, when the third liquid reaches the section of the first flow path, the collection flow path open/close valve may be closed and the bypass flow path open/close valve may be opened to start the second part of the third priming step and cause the third liquid to flow into the drip chamber. This mode is advantageous for reducing the likelihood that air mixes between the second liquid and the third liquid in the case where the whole quantity of the second liquid in the second container is administered to the patient, and subsequently the third liquid is sequentially administered to the patient.

A fifth infusion set of the present invention includes: a first flow path having, at one end, a first connector, which is to be connected to a first container for storing a first liquid, and having a downstream connector at another end; a first open/close valve, a drip chamber, and a variable valve that are provided in this order on the first flow path from the first connector side toward the downstream connector side; a second flow path having, at one end, a second connector, which is to be connected to a second container for storing a second liquid, another end of the second flow path being connected to a section of the first flow path between the first open/close valve and the drip chamber; a second open/close valve provided on the second flow path; a bypass flow path with one end in communication with a gas storing portion in the drip chamber, and another end in communication with a portion of the first flow path on the first connector side of the first open/close valve, or with the first connector; a bypass flow path open/close valve provided on the bypass flow path; a collection flow path with one end connected to a portion of the bypass flow path between the drip chamber and the bypass flow path open/close valve, the collection flow path having, at another end, a collection container connector, which is to be connected to a collection container; and a collection flow path open/close valve provided on the collection flow path.

A fifth priming method of the present invention for priming the fifth infusion set includes: a first priming step of causing the first liquid to flow from the first container into the first flow path and priming the first flow path using the first liquid; and a second priming step of causing the second liquid to flow from the second container into the second flow path and priming the second flow path using the second liquid. In the second priming step, the second liquid moves air that has been present in the second flow path toward the collection container through the gas storing portion in the drip chamber, the bypass flow path, and the collection flow path, or toward the first container through the gas storing portion in the drip chamber and the bypass flow path.

In the first priming step of the fifth priming method, the second open/close valve, the bypass flow path open/close valve, and the collection flow path open/close valve may be closed and the first open/close valve and the variable valve may be opened to cause the first liquid to flow from the first container toward the downstream connector. This is advantageous for priming the entire first flow path from the first connector to the downstream connector using the first liquid in a simply manner.

In the fifth priming method, after the first priming step, in a state where the first liquid is being caused to flow from the first container toward the downstream connector with the second open/close valve, the bypass flow path open/close valve, and the collection flow path open/close valve closed and with the first open/close valve and the variable valve opened, the first open/close valve and the variable valve may be closed, the second open/close valve may be opened, and the collection flow path open/close valve or the bypass flow path open/close valve may be opened to start the second priming step. Thus, drip injection of the first liquid can be readily switched to priming of the second flow path.

Preferably, the first open/close valve and the variable valve are closed when an interface between the first liquid and air that has flowed out, following the first liquid, from the first container reaches the section of the first flow path or when dripping of the first liquid in the drip chamber ends in a state where the first liquid is being caused to flow from the first container toward the downstream connector. This mode is advantageous for reducing the likelihood that air mixes between the first liquid and the second liquid in the case where the whole quantity of the first liquid in the first container is administered to a patient, and subsequently the second liquid is sequentially administered to the patient.

The fifth infusion set may further include: a third flow path having, at one end, a third connector, which is to be connected to a third container for storing a third liquid, another end of the third flow path being connected to the section of the first flow path; and a third open/close valve provided on the third flow path. The fifth priming method may further include a third priming step of causing the third liquid to flow from the third container into the third flow path and priming the third flow path using the third liquid. In the third priming step, the third liquid may move air that has been present in the third flow path toward the collection container through the gas storing portion in the drip chamber, the bypass flow path, and the collection flow path, or toward the first container through the gas storing portion in the drip chamber and the bypass flow path. Thus, the third flow path can be primed using the third liquid stored in the third container that is connected to the third flow path. In the case where the third liquid is a hazardous medical solution, it is unlikely that the third liquid or air that has come into contact therewith leaks out to the outside. For this reason, the operator can prime the third flow path using the third liquid without being exposed to the medicine.

In the third priming step of the fifth priming method, the third liquid may move air that has flowed out of the second container following the second liquid, toward the collection container through the gas storing portion in the drip chamber, the bypass flow path, and the collection flow path, or toward the first container through the gas storing portion in the drip chamber and the bypass flow path. This mode reduces the likelihood that, in the case where the second liquid is a hazardous medical solution, air that has come into contact with the second liquid leaks out to the outside.

In the fifth priming method, after the second priming step, when an interface between the second liquid and air that has flowed out, following the second liquid, from the second container reaches the section of the first flow path or when dripping of the second liquid in the drip chamber ends in a state where the second liquid is being flowed from the second container toward the downstream connector with the first open/close valve, the third open/close valve, the bypass flow path open/close valve, and the collection flow path open/close valve closed and with the second open/close valve and the variable valve opened, the second open/close valve and the variable valve may be closed, the third open/close valve may be opened, and the collection flow path open/close valve or the bypass flow path open/close valve may be opened to start the third priming step. This mode is advantageous for reducing the likelihood that air mixes between the second liquid and the third liquid in the case where the whole quantity of the second liquid in the second container is administered to a patient, and subsequently the third liquid is sequentially administered to the patient.

In the above-described first to fifth infusion sets of the present invention, the second connector may include a bar-shaped male member in which a flow path is formed, and a cover capable of being compressed and deformed in a longitudinal direction of the male member. When the second connector is connected to the second container, the cover may be compressed and deformed, and the male member may pass through the cover. When the second connector is separated from the second container, the cover may be restored to an initial state thereof and close a hole provided at or near a leading end of the male member and in communication with the flow path in the male member. According to this mode, even if the second connector is unintentionally separated from the second container, the likelihood that the second liquid leaks out to the outside can be reduced. This is advantageous for preventing the operator from being exposed to the medicine during priming in the case where the second liquid is a hazardous medical solution.

In the above-described first to fifth infusion sets of the present invention, the third connector may include a bar-shaped male member in which a flow path is formed, and a cover capable of being compressed and deformed in a longitudinal direction of the male member, similarly to the second connector. This is advantageous for preventing the operator from being exposed to the medicine during priming in the case where the third liquid is a hazardous medical solution.

Hereinafter, the present invention will be described in detail while illustrating preferable embodiments. Needless to say, however, the present invention is not limited to the following embodiments. The drawings that are referenced in the following description show main members that constitute the embodiments of the present invention in a simplified manner for convenience of description. Accordingly, the present invention may include any member that is not shown in the following diagrams. Also, members shown in the following diagrams may be changed or omitted within the scope of the present invention. In the drawings referenced in the description of the embodiments, members that correspond to members that are shown in a diagram referenced in a preceding embodiment are assigned the same reference signs as those in the drawing illustrating the preceding embodiment. Redundant descriptions of such members are omitted, and description of the preceding embodiment should be considered where appropriate.

Embodiment 1

FIG. 1 shows a schematic configuration of an infusion set 1 according to Embodiment 1 of the present invention. The infusion set 1 is used to sequentially administer, to a patient, a first liquid to a fourth liquid, which are stored respectively in a first container 20a to a fourth container 20d.

For example, the first liquid stored in the first container 20a may be a medical solution that contains a premedication, the second and third liquids stored in the second and third containers 20b and 20c may be hazardous medical solutions that contain an anti-cancer agent, and the fourth liquid stored in the fourth container 20d may be a physiological saline for washing out flow paths. The first container 20a to the fourth container 20d are sealed infusion bags, each of which is constituted by two soft sheets that are adhered to each other at their peripheral edge portions. The first container 20a to the fourth container 20d include ports 21a to 21d, respectively, for drawing out the stored liquids. Openings of the ports 21a to 21d are sealed by rubber plugs (which are not visible in FIG. 1). In addition to the aforementioned liquids, a small amount of air is stored in the first to fourth containers 20a to 20d. FIG. 1 only shows portions of the first to fourth containers 20a to 20d near the ports 21a to 21d.

The infusion set 1 includes a first flow path 10a, which serves as a main line. The first flow path 10a is constituted by a soft tube that is transparent and hollow. The first flow path 10a has a first connector 11a and a downstream connector 19 at an upstream end and a downstream end thereof, respectively. The first connector 11a and the downstream connector 19 are in communication with each other via the first flow path 10a. The first connector 11a is a puncture needle (which may also be called a spike) that has an acute tip, and is inserted into the rubber plug provided in the port 21a of the first container 20a. The downstream connector 19 is connected to a connector 32, which is provided at an upstream end of a soft tube 30. A needle 31, which is to be inserted into a patient's vein, is provided at a downstream end of the tube 30.

A first open/close valve 12a, a drip chamber 14, and a variable valve 17 are provided in this order from the first connector 11a side toward the downstream connector 19 side, on the first flow path 10a. The first open/close valve 12a switches between a state of allowing a liquid in the first flow path 10a to flow and a state of not allowing this liquid to flow, by opening and closing the first flow path 10a. Although the first open/close valve 12a is not limited, but may be a clamp that is known in the medical field, for example. The drip chamber 14 makes flowing of a liquid through the first flow path 10a visible. The variable valve 17 adjusts the flow rate of the liquid flowing through the first flow path 10a by compressing the first flow path 10a in a diameter direction and adjusting the cross-sectional area of the first flow path 10a. Although the variable valve 17 is not limited, but may be a roller clip that is known in the medical field, for example.

The infusion set 1 also includes a second flow path 10b, a third flow path 10c, and a fourth flow path 10d, which serve as side-injection lines. The second to fourth flow paths 10b to 10d are constituted by soft tubes that are transparent and hollow, similarly to the first flow path 10a. The second, third, and fourth flow paths 10b, 10c, and 10d have second, third, and fourth connectors 11b, 11c, and 11d, respectively, at their upstream ends. The second to fourth connectors 11b to 11d are lever lock connectors each including a male member and a lock lever with a claw (e.g. see Patent Document 2). The second to fourth connectors 11b to 11d are connected to the ports 21b to 21d of the second to fourth containers 20b to 20d via adapters 22b to 22d, respectively. Each of the adapters 22b to 22d includes a puncture needle, which has an acute tip capable of being inserted into a corresponding one of the rubber plugs in the ports 21b to 21d, an engaging claw, which is to engage with a corresponding one of the ports 21b to 21d, and a mixture injection port, which has an elastic partition member called a septum (e.g. see Patent Document 3). The male members of the second to fourth connectors 11b to 11d are inserted into the elastic partition members of the mixture injection ports, and the claws of the second to fourth connectors 11b to 11d engage with the mixture injection ports of the ports 21b to 21d. Connecting the second to fourth flow paths 10b to 10d to the ports 21b to 21d via the second to fourth connectors 11b to 11d and the adapters 22b to 22d is advantageous in reducing the likelihood of a hazardous medicine, such as an anti-cancer agent, leaking out to the outside and an operator being exposed to the medicine.

The second to fourth flow paths 10b to 10d are brought into communication with a section of the first flow path 10a between the first open/close valve 12a and the drip chamber 14 (this section will be referred to as a "branch section"). In FIG. 1, one branch flow path 10x branches from a first branching portion 18a, which is provided on the first flow path 10a and has a T-shape (or a Y-shape), second and third branching portions 18b and 18c, which have a T-shape (or a Y-shape), are provided in this order on the branch flow path 10x, a second flow path 10b branches from the second branching portion 18b, and a third flow path 10c and a fourth flow path 10d branch from the third branching portion 18c. In the present invention, the second to fourth flow paths (side-injection lines) 10b to 10d mean portions from the second to fourth connectors 11b to 11d, respectively, to the first flow path (main line) 10a. Accordingly, in the configuration in FIG. 1, each of the second to fourth flow paths 10b to 10d has a flow path portion that is shared with the other flow paths, and a unique flow path portion that is distinguished from the other flow paths.

Second, third, and fourth open/close valves 12b, 12c, and 12d are provided on the second, third, and fourth flow paths 10b, 10c, and 10d, respectively. As shown in FIG. 1, if the second to fourth flow paths 10b to 10d have, as a portion thereof, a flow path portion shared by the other flow paths, the second to fourth open/close valves 12b to 12d are provided in unique flow path portions of the second to fourth flow paths 10b to 10d that are distinguished from the other flow paths. The second to fourth open/close valves 12b to 12d switch between a state of allowing liquids in the second to fourth flow paths 10b to 10d to flow and a state of not allowing the liquids to flow by opening and closing the second to fourth flow paths 10b to 10d, similarly to the first open/close valve 12a. The second to fourth open/close valves 12b to 12d are not limited, but may be clamps that are known in the medical field, for example.

A description will be given of a priming method for the infusion set 1 according to Embodiment 1 that is configured as described above. All operations in the following priming method are manually performed by an operator. However, some of the operations may be automatically performed. Similar to general infusion, the first to fourth liquids flow in the infusion set 1 using gravity.

The first container 20a to the fourth container 20d, in which the first liquid to the fourth liquid are stored, respectively, are suspended from, for example, an irrigator stand (not shown), with the ports 21a to 21d facing downward. The adapters 22b to 22d are attached to the ports 21b to 21d.

An infusion set 1 with the first to fourth open/close valves 12a to 12d and the variable valve 17 in a closed state is prepared. The first connector 11a in the infusion set 1 is connected to the port 21a of the first container 20a, and the second to fourth connectors 11b to 11d in the infusion set 1 are connected to the adapters 22b to 22d, respectively. The first flow path 10a is suspended in a substantially vertical direction due to gravity such that the first connector 11a, the first open/close valve 12a, the drip chamber 14, and the variable valve 17 are arranged in this order from the upper side toward the lower side. The second to fourth containers 20b to 20d are arranged at positions higher than the first open/close valve 12a. The downstream connector 19 is connected to the connector 32.

Initially, the first flow path 10a is primed using the first liquid (e.g. a premedication) in the first container 20a. That is to say, the first open/close valve 12a and the variable valve 17 are opened. The first liquid in the first container 20a flows from the first connector 11a into the first flow path 10a. When the first liquid reaches the tip of the needle 31 that is provided further downstream of the downstream connector 19, the first open/close valve 12a and/or the variable valve 17 are closed once. A flow path that extends from the first container 20a to the needle 31 through the first flow path 10a and the tube 30 is filled with the first liquid.

Next, the needle 31 is inserted into a patient's vein.

Next, the first open/close valve 12a and the variable valve 17 are opened again. A drip of the first liquid is started. The flow rate of the first liquid can be checked in the drip chamber 14. The opening of the variable valve 17 is adjusted such that the flow rate of the first liquid takes a predetermined value.

Upon the first liquid in the first container 20a running out, air in the first container 20a flows out, following the first liquid, from the port 21a into the first flow path 10a. An interface (gas-liquid interface or liquid surface) between the first liquid and the air moves down in the first flow path 10a.

When the gas-liquid interface reaches the first branching portion 18a, the variable valve 17 is closed. The drip of the first liquid is temporarily discontinued. A portion from the first branching portion 18a to the first container 20a is filled with the air that has flowed out of the first container 20a, and a portion on the downstream side (on the downstream connector 19 side) of the first branching portion 18a is filled with the first liquid.

Next, the second open/close valve 12b is opened. The second liquid in the second container 20b flows into the second flow path 10b. Since the variable valve 17 and the third and fourth open/close valves 12c and 12d are closed, the second liquid moves air that has been present in the second flow path 10b toward the first container 20a through the first branching portion 18a and the first flow path 10a in this order.

When an interface (gas-liquid interface or liquid surface) between the air and the second liquid reaches the first branching portion 18a, the first open/close valve 12a is closed, and the variable valve 17 is opened. The second liquid moves down the first flow path 10a through the first branching portion 18a, and flows toward the downstream connector 19. Thus, the drip of the first liquid remaining in the first flow path 10a is resumed, and subsequently, a drip of the second liquid is started. The flow rate of the second liquid can be checked in the drip chamber 14. The opening of the variable valve 17 is adjusted such that the flow rate of the second liquid takes a predetermined value. Air that has been present in the second flow path 10b before opening the second open/close valve 12b is confined to a portion of the first flow path 10a on the upstream side (on the first container 20a side) of the first branching portion 18a, and the first container 20a.

Upon the second liquid in the second container 20b running out, air in the second container 20b flows out, following the second liquid, from the port 21b into the second flow path 10b. An interface (gas-liquid interface or liquid surface) between the second liquid and the air moves down in the second flow path 10b. When the gas-liquid interface reaches the first branching portion 18a, the second open/close valve 12b and the variable valve 17 are closed. The drip of the second liquid is temporarily discontinued. A portion from the first branching portion 18a to the second container 20b is filled with the air that has flowed out of the second container 20b, and a portion on the downstream side (on the downstream connector 19 side) of the first branching portion 18a is filled with the second liquid.

Next, the first open/close valve 12a and the third open/close valve 12c are opened. The third liquid in the third container 20c flows into the third flow path 10c. Since the variable valve 17 and the second and fourth open/close valves 12b and 12d are closed, the third liquid moves air that has been present in the third flow path 10c toward the first container 20a through the first branching portion 18a and the first flow path 10a in this order.

When an interface (gas-liquid interface or liquid surface) between the air and the third liquid reaches the first branching portion 18a, the first open/close valve 12a is closed, and the variable valve 17 is opened. The third liquid moves down the first flow path 10a through the first branching portion 18a, and flows toward the downstream connector 19. Thus, the drip of the second liquid remaining in the first flow path 10a is resumed, and subsequently, a drip of the third liquid is started. The flow rate of the third liquid can be checked in the drip chamber 14. The opening of the variable valve 17 is adjusted such that the flow rate of the third liquid takes a predetermined value. Air that has been present in the third flow path 10c before opening the third open/close valve 12c is confined to a portion of the first flow path 10a on the upstream side (on the first container 20a side) of the first branching portion 18a, and the first container 20a.

Then, the fourth flow path 10d is primed using the fourth liquid in the fourth container 20d, and subsequently a drip of the fourth liquid is given, in accordance with the same procedure. After the fourth liquid in the fourth container 20d has run out, the fourth open/close valve 12d and the variable valve 17 are closed. The drips of the first liquid to the fourth liquid thus end. The needle 31 is pulled out of the patient. The infusion set 1 is discarded with the first container 20a to the fourth container 20d and the tube 30 connected thereto.

As described above, with the infusion set 1 according to Embodiment 1, the side-injection lines (second to fourth flow paths 10b to 10d) are primed, line-by-line, after a drip of the first liquid has started and immediately before a drip of the liquids (second liquid to fourth liquids) corresponding to the respective side-injection lines starts. Furthermore, the liquids stored in the container connected to the respective side-injection lines are used as priming solutions for the side-injection lines.

When priming is performed for an infusion set in which at least one side-injection line branches from one main line, such as the infusion set 1 according to Embodiment 1, conventionally, a method called back-priming (also referred to as "priming-back") is often employed in which, for the side-injection line, a priming solution is caused to flow back from the main line to the side-injection line. Back-priming needs to be performed before a container is connected to the side-injection line. If, after the container has been connected to the side-injection line, air remaining in a portion of a flow path of the infusion set is found, it is necessary to remove the container from the side-injection line and perform back-priming again, making the operation complex. In addition, if back-priming is performed, the entire infusion set including the main line and the side-injection line is filled with the same priming solution. Accordingly, in the case of giving a drip of a liquid in the container connected to the side-injection line to the patient, a drip of the priming solution is necessarily given before the drip of the liquid.

In the priming method for the infusion set 1 according to Embodiment 1, priming is performed after the containers (first to fourth containers 20a to 20d) have been connected to all of the main line (first flow path 10a) and the side-injection lines (second to fourth flow paths 10b to 10d). Moreover, the main line and the side-injection lines are primed immediately before a drip of the liquid in the container connected to each of those lines is given. Since priming is performed line-by-line, operational errors, such as air remaining in a line being overlooked, are unlikely to occur.

In Embodiment 1, the side-injection lines (second to fourth flow paths 10b to 10d) are primed using the liquids stored in the containers that are connected to the respective side-injection lines. Accordingly, in the case of sequentially giving drips of the first to fourth liquids, the problem does not occur that a drip of a priming solution used in common is necessarily given before the drip of each liquid as with the conventional technique.

If the liquids (second and third liquids) stored in the containers (second and third containers 20b and 20c) connected to the side-injection lines (second and third flow paths 10b and 10c) are hazardous medical solutions such as an anti-cancer agent, there is a possibility that air that has come into contact with these hazardous medical solutions contain vapor of the hazardous medical solutions. In Embodiment 1, air that has been present in the side-injection lines (second and third flow paths 10b and 10c) before being primed is confined to the infusion set 1 and the first container 20a due to priming of these side-injection lines (second and third flow paths 10b and 10c) and does not leak out to the outside. In addition, air that has flowed out, following the liquids (second and third liquids), from the containers (second and third containers 20b and 20c) to the side-injection lines (second and third flow paths 10b and 10c) is also confined to the infusion set 1 and the first container 20a due to priming of other side-injection lines (third and fourth flow paths 10c and 10d) that is to be performed immediately after the outflow of the air, and does not leak out to the outside. Thus, in Embodiment 1, even if a side-injection line is primed using a hazardous medical solution, the hazardous medical solution and vapor thereof do not leak out to the outside. This is advantageous for reducing the likelihood that the operator who performs priming is exposed to the medicine.

In the above-described priming method for the infusion set 1, the variable valve 17 is switched to an open or closed state when an interface (gas-liquid interface) between any of the first to fourth liquids and air reaches the first branching portion 18a. However, in the present invention, the time when the gas-liquid interface reaches the first branching portion 18a need not accurately coincide with the time when the variable valve 17 is switched. Commonly, the variable valve 17 need only be switched to an open or close state when the gas-liquid interface reaches a section (branch section) of the first flow path 10a between the first open/close valve 12a and the drip chamber 14.

Embodiment 2

Figure 2:
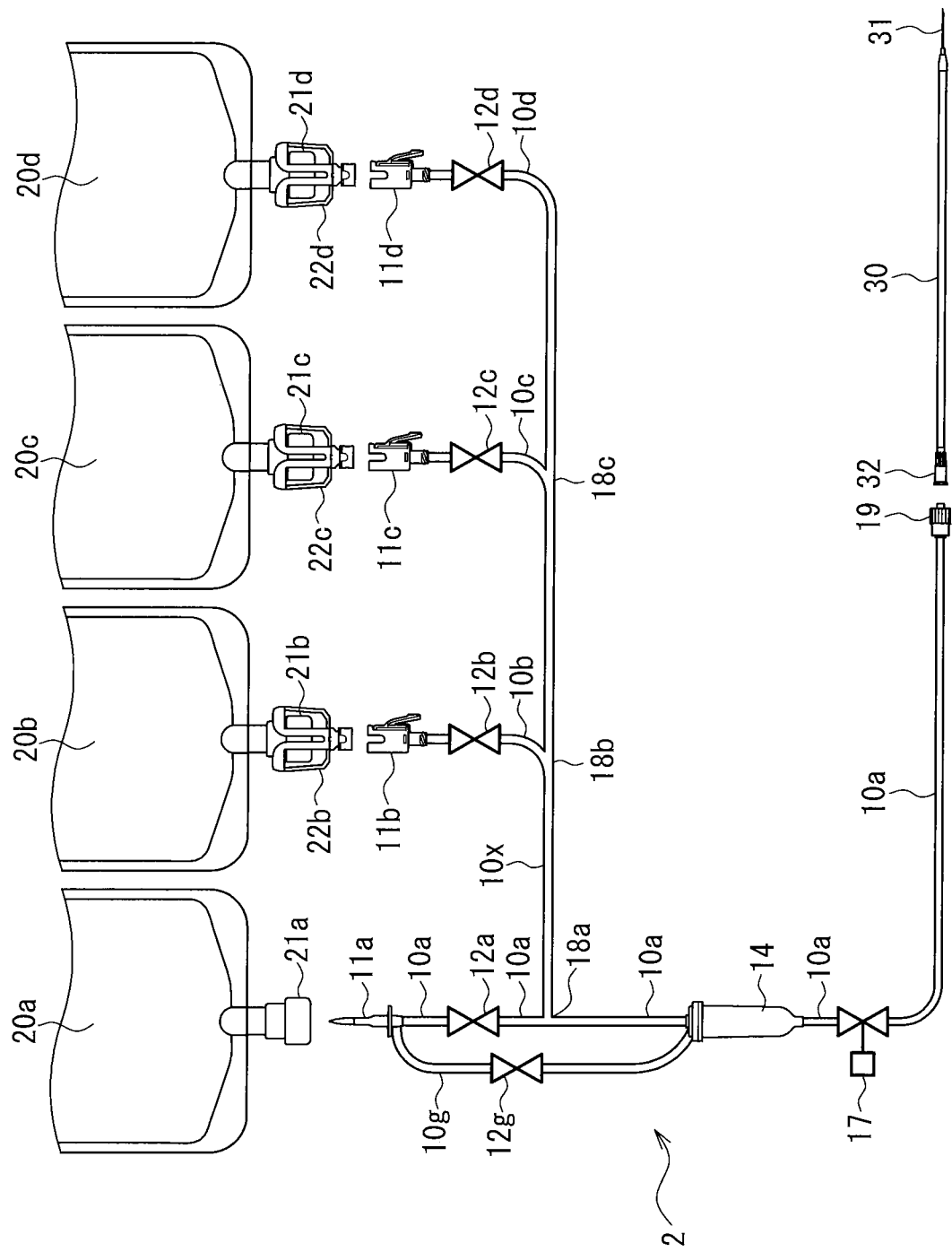
FIG. 2 shows an infusion set according to Embodiment 2 of the present invention.

An infusion set 2 and a priming method for the infusion set 2 according to Embodiment 2 of the present invention will be described, mainly regarding differences from Embodiment 1. FIG. 2 shows a schematic configuration of the infusion set 2. The infusion set 2 includes a bypass flow path 10g that brings a gas storing portion of the drip chamber 14 into communication with a portion of the first flow path 10a on the upstream side (on the first connector 11a side) of the first open/close valve 12a or the first connector 11a, and an open/close valve (bypass flow path open/close valve) 12g that is provided on the bypass flow path 10g.

The bypass flow path 10g is not limited, but may be constituted by a hollow, soft tube, similarly to the first to fourth flow paths 10a to 10d. A lower end of the bypass flow path 10g is brought into communication with a portion in which air is present above a liquid surface in the drip chamber 14 (this portion will be called a gas storing portion). Ordinarily, the drip chamber 14 is constituted by a chamber in which a liquid is stored and that is transparent and has a cylindrical shape, and a cap for closing an opening at an upper end of the chamber. In the infusion set 2 in FIG. 2, a lower end of the bypass flow path 10g is connected to the cap. As long as the bypass flow path 10g is in communication with the gas storing portion in the drip chamber 14, the lower end of the bypass flow path 10g may be connected to the chamber. The bypass flow path 10g brings the gas storing portion in the drip chamber 14 into communication with a portion of the first flow path 10a on the upstream side (on the first container 20a side) of the first open/close valve 12a, when the first open/close valve 12a is closed. In the infusion set 2 in FIG. 2, an upper end of the bypass flow path 10g is connected to a base end of the first connector 11a, but may alternatively be connected to a portion of the first flow path 10a between the first open/close valve 12a and the first connector 11a.

The open/close valve 12g is not limited, but may be a clamp that is known in the medical field, similarly to the first to fourth open/close valves 12a to 12d.

A description will be given of a priming method for the infusion set 2 according to Embodiment 2 that is configured as described above.

The first container 20a to the fourth container 20d, in which the first liquid to the fourth liquid are stored, respectively, are suspended from, for example, an irrigator stand (not shown), with the ports 21a to 21d facing downward. The adapters 22b to 22d are attached to the ports 21b to 21d.

An infusion set 2 with the first to fourth open/close valves 12a to 12d, the open/close valve 12g, and the variable valve 17 in a closed state is prepared. The first connector 11a in the infusion set 2 is connected to the port 21a of the first container 20a, and the second to fourth connectors 11b to 11d in the infusion set 2 are connected to the adapters 22b to 22d, respectively. The first flow path 10a is suspended in a substantially vertical direction due to gravity such that the first connector 11a, the first open/close valve 12a, the drip chamber 14, and the variable valve 17 are arranged in this order from the upper side toward the lower side. The second to fourth containers 20b to 20d are arranged at positions higher than the first open/close valve 12a. The downstream connector 19 is connected to the connector 32.

Initially, the first flow path 10a is primed using the first liquid (e.g. a premedication) in the first container 20a. That is to say, the first open/close valve 12a and the variable valve 17 are opened. The first liquid in the first container 20a flows from the first connector 11a into the first flow path 10a. When the first liquid reaches the tip of the needle 31 that is provided further downstream of the downstream connector 19, the first open/close valve 12a and/or the variable valve 17 are closed once. A flow path that extends from the first container 20a to the needle 31 through the first flow path 10a and the tube 30 is filled with the first liquid.

Next, the needle 31 is inserted into a patient's vein.

Next, the first open/close valve 12a and the variable valve 17 are opened again. A drip of the first liquid is started. The flow rate of the first liquid can be checked in the drip chamber 14. The opening of the variable valve 17 is adjusted such that the flow rate of the first liquid takes a predetermined value. It is checked that the liquid surface in the drip chamber 14 is at a predetermined height (position).

Upon the first liquid in the first container 20a running out, air in the first container 20a flows out, following the first liquid, from the port 21a into the first flow path 10a. An interface (gas-liquid interface or liquid surface) between the first liquid and the air moves down in the first flow path 10a. When dripping of the first liquid in the drip chamber 14 ends, the first open/close valve 12a and the variable valve 17 are closed. The drip of the first liquid is temporarily discontinued. A portion from the gas storing portion in the drip chamber 14 to the first container 20a is filled with the air that has flowed out of the first container 20a, and a portion on the downstream side (on the downstream connector 19 side) of the liquid surface in the drip chamber 14 is filled with the first liquid.

Next, the open/close valve 12g and the second open/close valve 12b are opened. The second liquid in the second container 20b flows into the second flow path 10b. Since the variable valve 17 and the first, third, and fourth open/close valves 12a, 12c, and 12d are closed, the second liquid moves air that has been present in the second flow path 10b toward the first container 20a through the first branching portion 18a, the first flow path 10a, the drip chamber 14, and the bypass flow path 10g in this order. The second liquid flows into the drip chamber 14 through the first branching portion 18a and the first flow path 10a in this order. After checking that dripping of the second liquid has started in the drip chamber 14, the open/close valve 12g is closed, and the variable valve 17 is opened. Thereafter, the second liquid moves down the first flow path 10a, and flows toward the downstream connector 19. Thus, the drip of the first liquid remaining in the first flow path 10a is resumed, and subsequently, a drip of the second liquid is started. The flow rate of the second liquid can be checked in the drip chamber 14. The opening of the variable valve 17 is adjusted such that the flow rate of the second liquid takes a predetermined value. It is checked that the liquid surface in the drip chamber 14 is at a predetermined height (position). Air that has been present in the second flow path 10b before the second open/close valve 12b is opened is confined to the gas storing portion in the drip chamber 14, the bypass flow path 10g, and the first container 20a.

Upon the second liquid in the second container 20b running out, air in the second container 20b flows out, following the second liquid, from the port 21b into the second flow path 10b. An interface (gas-liquid interface or liquid surface) between the second liquid and the air moves down in the second flow path 10b. When dripping of the second liquid in the drip chamber 14 ends, the second open/close valve 12b and the variable valve 17 are closed. The drip of the second liquid is temporarily discontinued. A portion from the gas storing portion in the drip chamber 14 to the second container 20b is filled with the air that has flowed out of the second container 20b, and a portion on the downstream side (on the downstream connector 19 side) of the liquid surface in the drip chamber 14 is filled with the second liquid.

Next, the open/close valve 12g and the third open/close valve 12c are opened. The third liquid in the third container 20c flows into the third flow path 10c. Since the variable valve 17 and the first, second, and fourth open/close valves 12a, 12b, and 12d are closed, the third liquid moves air that has been present in the third flow path 10c toward the first container 20a through the first branching portion 18a, the first flow path 10a, the drip chamber 14, and the bypass flow path 10g in this order. The third liquid flows into the drip chamber 14 through the first branching portion 18a and the first flow path 10a in this order. After checking that dripping of the third liquid has started in the drip chamber 14, the open/close valve 12g is closed, and the variable valve 17 is opened. Thereafter, the third liquid moves down the first flow path 10a, and flows toward the downstream connector 19. Thus, the drip of the second liquid remaining in the first flow path 10a is resumed, and subsequently, a drip of the third liquid is started. The flow rate of the third liquid can be checked in the drip chamber 14. The opening of the variable valve 17 is adjusted such that the flow rate of the third liquid takes a predetermined value. It is checked that the liquid surface in the drip chamber 14 is at a predetermined height (position). Air that has been present in the third flow path 10c before the third open/close valve 12c is opened is confined to the gas storing portion in the drip chamber 14, the bypass flow path 10g, and the first container 20a.

Then, the fourth flow path 10d is primed using the fourth liquid in the fourth container 20d, and subsequently a drip of the fourth liquid is given, in accordance with the same procedure. After the fourth liquid in the fourth container 20d has run out, the fourth open/close valve 12d and the variable valve 17 are closed. The drips of the first liquid to the fourth liquid thus end. The needle 31 is pulled out of the patient. The infusion set 2 is discarded with the first container 20a to the fourth container 20d and the tube 30 connected thereto.

Similarly to Embodiment 1, with the infusion set 2 according to Embodiment 2, the side-injection lines (second to fourth flow paths 10b to 10d) are primed, line-by-line, after a drip of the first liquid has started and immediately before a drip of the liquids (second liquid to fourth liquids) corresponding to the respective side-injection lines starts. Furthermore, the liquids stored in the container connected to the respective side-injection lines are used as priming solutions for the side-injection lines.

Air that has been present in the side-injection lines (second and third flow paths 10b and 10c) before being primed is confined to the infusion set 2 and the first container 20a due to priming of these side-injection lines (second and third flow paths 10b and 10c) and does not leak out to the outside. In addition, air that has flowed out, following the liquids (second and third liquids), from the containers (second and third containers 20b and 20c) to the side-injection lines (second and third flow paths 10b and 10c) is also confined to the infusion set 2 and the first container 20a due to priming of other side-injection lines (third and fourth flow paths 10c and 10d) that is to be performed immediately after the outflow of the air, and does not leak out to the outside. Even if a side-injection line is primed using a hazardous medical solution, the hazardous medical solution and vapor thereof do not leak out to the outside. This is advantageous for reducing the likelihood that the operator who performs priming is exposed to the medicine.

In the above-described priming method for the infusion set 2, the first to fourth open/close valves 12a to 12d and the variable valve 17 are closed when dripping of the first to fourth liquids ends in the drip chamber 14. However, in the present invention, the time when dripping of the first to fourth liquids ends in the drip chamber 14 need not accurately coincide with the time when the valves 12a to 12d and 17 are closed. The valves 12a to 12d and 17 may be closed before dripping in the drip chamber 14 ends. Specifically, the valves 12a to 12d and 17 may be closed when an interface (gas-liquid interface) between any of the first to fourth liquids and the following air reaches a section (branch section) of the first flow path 10a between the first open/close valve 12a and the drip chamber 14.

Embodiment 2 is the same as Embodiment 1, except for the above-described configuration. The descriptions of Embodiment 1 also apply to Embodiment 2 as appropriate.

Embodiment 3

Figure 3:
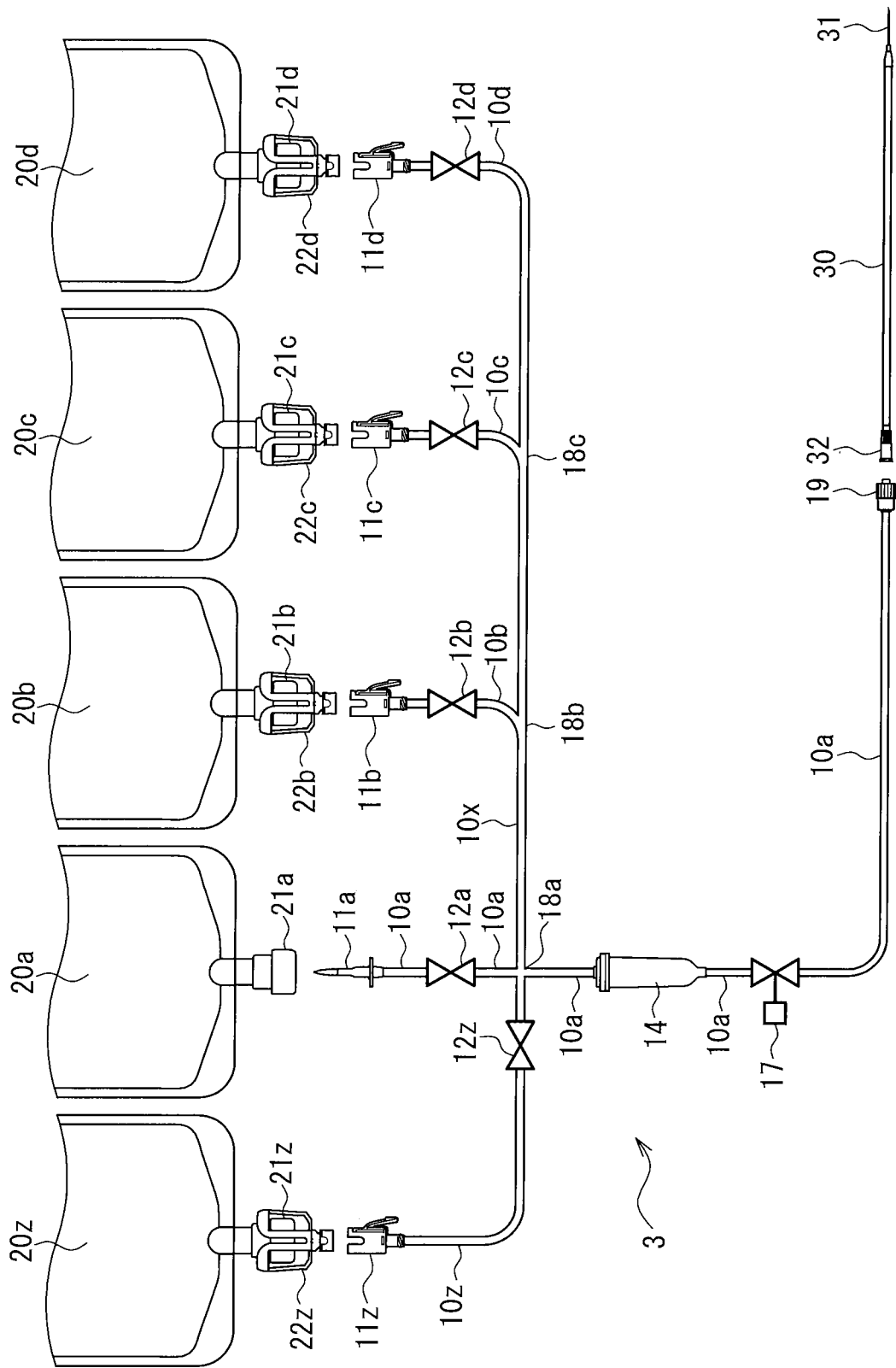
FIG. 3 shows an infusion set according to Embodiment 3 of the present invention.

An infusion set 3 and a priming method for the infusion set 3 according to Embodiment 3 of the present invention will be described, mainly regarding differences from Embodiments 1 and 2. FIG. 3 shows a schematic configuration of the infusion set 3. The infusion set 3 includes a collection container 20z and a collection flow path 10z.

The collection container 20z is a sealed container, and it is preferable that the shape thereof changes in accordance with the amount of content (gas) in the collection container 20z. The collection container 20z is not limited, but may be, for example, a bag constituted by two soft sheets that are adhered to each other at their peripheral edge portions, similarly to the first container 20a to the fourth container 20d. The collection container 20z includes a port 21z. An opening of the port 21z is sealed by a rubber plug (which is not visible in FIG. 3).

The collection flow path 10z constitutes a collection line that brings the collection container 20z into communication with the first flow path 10a (main line). The collection flow path 10z is constituted by a hollow, soft tube, similarly to the first to fourth flow paths 10a to 10d. One end of the collection flow path 10z is in communication with the first branching portion 18a, and the other end of the collection flow path 10z is provided with a connector (collection container connector) 11z. The connector 11z is connected to the port 21z of the collection container 20z via an adapter (collection container adapter) 22z. The connector 11z is a lever lock connector that is the same as the second to fourth connectors 11b to 11d (e.g. see Patent Document 2). The adapter 22z is the same as the second to fourth adapters 22b to 22d (e.g. see Patent Document 3).

An open/close valve (collection flow path open/close valve) 12z is provided on the collection flow path 10z. The open/close valve 12z switches between a state of allowing a gas in the collection flow path 10z to flow and a state of not allowing the gas to flow by opening and closing the collection flow path 10z, similarly to the first to fourth open/close valves 12a to 12d. Although the open/close valve 12z is not limited, but may be a clamp that is known in the medical field, for example.

A description will be given of a priming method for the infusion set 3 according to Embodiment 3 that is configured as described above.

The first container 20a to the fourth container 20d, in which the first liquid to the fourth liquid are stored, respectively, are suspended from, for example, an irrigator stand (not shown), with the ports 21a to 21d facing downward. The adapters 22b to 22d are attached to the ports 21b to 21d.

An infusion set 3 with the first to fourth open/close valves 12a to 12d, the open/close valve 12z, and the variable valve 17 in a closed state is prepared. Also, an empty collection container 20z with the port 21z to which the adapter 22z is attached is prepared. The first connector 11a in the infusion set 3 is connected to the port 21a of the first container 20a, the second to fourth connectors 11b to 11d in the infusion set 3 are connected to the adapters 22b to 22d, respectively, and the connector 11z is connected to the adapter 22z. The first flow path 10a is suspended in a substantially vertical direction due to gravity such that the first connector 11a, the first open/close valve 12a, the drip chamber 14, and the variable valve 17 are arranged in this order from the upper side toward the lower side. The second to fourth containers 20b to 20d are arranged at positions higher than the first open/close valve 12a. The downstream connector 19 is connected to the connector 32.

Initially, the first flow path 10a is primed using the first liquid (e.g. a premedication) in the first container 20a. That is to say, the first open/close valve 12a and the variable valve 17 are opened. The first liquid in the first container 20a flows from the first connector 11a into the first flow path 10a. When the first liquid reaches the tip of the needle 31 that is provided further downstream of the downstream connector 19, the first open/close valve 12a and/or the variable valve 17 are closed once. A flow path that extends from the first container 20a to the needle 31 through the first flow path 10a and the tube 30 is filled with the first liquid.

Next, the needle 31 is inserted into a patient's vein.

Next, the first open/close valve 12a and the variable valve 17 are opened again. A drip of the first liquid is started. The flow rate of the first liquid can be checked in the drip chamber 14. The opening of the variable valve 17 is adjusted such that the flow rate of the first liquid takes a predetermined value.

Upon the first liquid in the first container 20a running out, air in the first container 20a flows out, following the first liquid, from the port 21a into the first flow path 10a. An interface (gas-liquid interface or liquid surface) between the first liquid and the air moves down in the first flow path 10a. When the gas-liquid interface reaches the first branching portion 18a, the first open/close valve 12a and the variable valve 17 are closed. The drip of the first liquid is temporarily discontinued. A portion from the first branching portion 18a to the first container 20a is filled with the air that has flowed out of the first container 20a, and a portion on the downstream side (on the downstream connector 19 side) of the first branching portion 18a is filled with the first liquid.

Next, the open/close valve 12z and the second open/close valve 12b are opened. The second liquid in the second container 20b flows into the second flow path 10b. Since the variable valve 17 and the first, third, and fourth open/close valves 12a, 12c, and 12d are closed, the second liquid moves air that has been present in the second flow path 10b toward the collection container 20z through the first branching portion 18a, and the collection flow path 10z in this order.

When an interface (gas-liquid interface or liquid surface) between the air and the second liquid reaches the first branching portion 18a, the open/close valve 12z is closed, and the variable valve 17 is opened. The second liquid moves down the first flow path 10a through the first branching portion 18a, and flows toward the downstream connector 19. Thus, the drip of the first liquid remaining in the first flow path 10a is resumed, and subsequently, a drip of the second liquid is started. The flow rate of the second liquid can be checked in the drip chamber 14. The opening of the variable valve 17 is adjusted such that the flow rate of the second liquid takes a predetermined value. Air that has been present in the second flow path 10b before opening the second open/close valve 12b is confined to the collection flow path 10z and the collection container 20z.

Upon the second liquid in the second container 20b running out, air in the second container 20b flows out, following the second liquid, from the port 21b into the second flow path 10b. An interface (gas-liquid interface or liquid surface) between the second liquid and the air moves down in the second flow path 10b. When the gas-liquid interface reaches the first branching portion 18a, the second open/close valve 12b and the variable valve 17 are closed. The drip of the second liquid is temporarily discontinued. A portion from the first branching portion 18a to the second container 20b is filled with the air that has flowed out of the second container 20b, and a portion on the downstream side (on the downstream connector 19 side) of the first branching portion 18a is filled with the second liquid.

Next, the open/close valve 12z and the third open/close valve 12c are opened. The third liquid in the third container 20c flows into the third flow path 10c. Since the variable valve 17 and the first, second, and fourth open/close valves 12a, 12b, and 12d are closed, the third liquid moves air that has been present in the third flow path 10c toward the collection container 20z through the first branching portion 18a and the collection flow path 10z in this order.

When an interface (gas-liquid interface or liquid surface) between the air and the third liquid reaches the first branching portion 18a, the open/close valve 12z is closed, and the variable valve 17 is opened. The third liquid moves down the first flow path 10a through the first branching portion 18a, and flows toward the downstream connector 19. Thus, the drip of the second liquid remaining in the first flow path 10a is resumed, and subsequently, a drip of the third liquid is started. The flow rate of the third liquid can be checked in the drip chamber 14. The opening of the variable valve 17 is adjusted such that the flow rate of the third liquid takes a predetermined value. Air that has been present in the third flow path 10c before opening the third open/close valve 12c is confined to the collection flow path 10z and the collection container 20z.

Then, the fourth flow path 10d is primed using the fourth liquid in the fourth container 20d, and subsequently a drip of the fourth liquid is given, in accordance with the same procedure. After the fourth liquid in the fourth container 20d has run out, the fourth open/close valve 12d and the variable valve 17 are closed. The drips of the first liquid to the fourth liquid thus end. The needle 31 is pulled out of the patient. The infusion set 3 is discarded with the first container 20a to the fourth container 20d, the collection container 20z, and the tube 30 connected thereto.

Similarly to Embodiment 1, with the infusion set 2 according to Embodiment 3, the side-injection lines (second to fourth flow paths 10b to 10d) are primed, line-by-line, after a drip of the first liquid has started and immediately before a drip of the liquids (second liquid to fourth liquids) corresponding to the respective side-injection lines starts. Furthermore, the liquids stored in the container connected to the respective side-injection lines are used as priming solutions for the side-injection lines.

Air that has been present in the side-injection lines (second and third flow paths 10b and 10c) before being primed is confined to the infusion set 3 and the collection container 20z due to priming of these side-injection lines (second and third flow paths 10b and 10c) and does not leak out to the outside. In addition, air that has flowed out, following the liquids (second and third liquids), from the containers (second and third containers 20b and 20c) to the side-injection lines (second and third flow paths 10b and 10c) is also confined to the infusion set 3 and the collection container 20z due to priming of other side-injection lines (third and fourth flow paths 10c and 10d) that is to be performed immediately after the outflow of the air, and does not leak out to the outside. Even if a side-injection line is primed using a hazardous medical solution, the hazardous medical solution and vapor thereof do not leak out to the outside. This is advantageous for reducing the likelihood that the operator who performs priming is exposed to the medicine.

Air that has been discharged from the side-injection lines due to priming is collected into the first container 20a in Embodiments 1 and 2, whereas, in Embodiment 3, discharged air is collected into the dedicated collection container 20z. The collection container 20z need not have the same configuration as the first container 20a to the fourth container 20d, and may be modified in any manner to have a configuration appropriate for collecting air, for example. A container that has a capacity corresponding to the flow path volume of the side-injection lines can be selected as the collection container 20z. The configuration of the collection line that brings the collection container 20z into communication with the first branching portion 18a is not limited to that shown in FIG. 3 either. A configuration may alternatively be employed in which the adapter 22z and the connector 11z are omitted, and the tube that constitutes the collection flow path 10z is directly connected to the collection container 20z. In this case, a terminal of the tube connected to the collection container 20z corresponds to the collection container connector.

In the above-described priming method for the infusion set 3, the first to fourth open/close valves 12a to 12d and the variable valve 17 are closed when an interface (gas-liquid interface) between the first to fourth liquids and air that has been present in the first to fourth containers 20a to 20d reaches the first branching portion 18a, respectively. However, in the present invention, the time when the gas-liquid interface reaches the first branching portion 18a need not accurately coincide with the time when the valves 12a to 12d and 17 are closed. Commonly, the valves 12a to 12d and 17 need only be closed when the gas-liquid interface reaches a section (branch section) between the first open/close valve 12a and the drip chamber 14.

In FIG. 3, the collection flow path 10z is connected to the first branching portion 18a, but the present invention is not limited thereto. The collection flow path 10z need only be connected to a section (branch section) of the first flow path 10a between the first open/close valve 12a and the drip chamber 14.

Embodiment 3 is the same as Embodiments 1 and 2, except for the above-described configuration. The descriptions of Embodiments 1 and 2 also apply to Embodiment 3.

Embodiment 4

Figure 4:
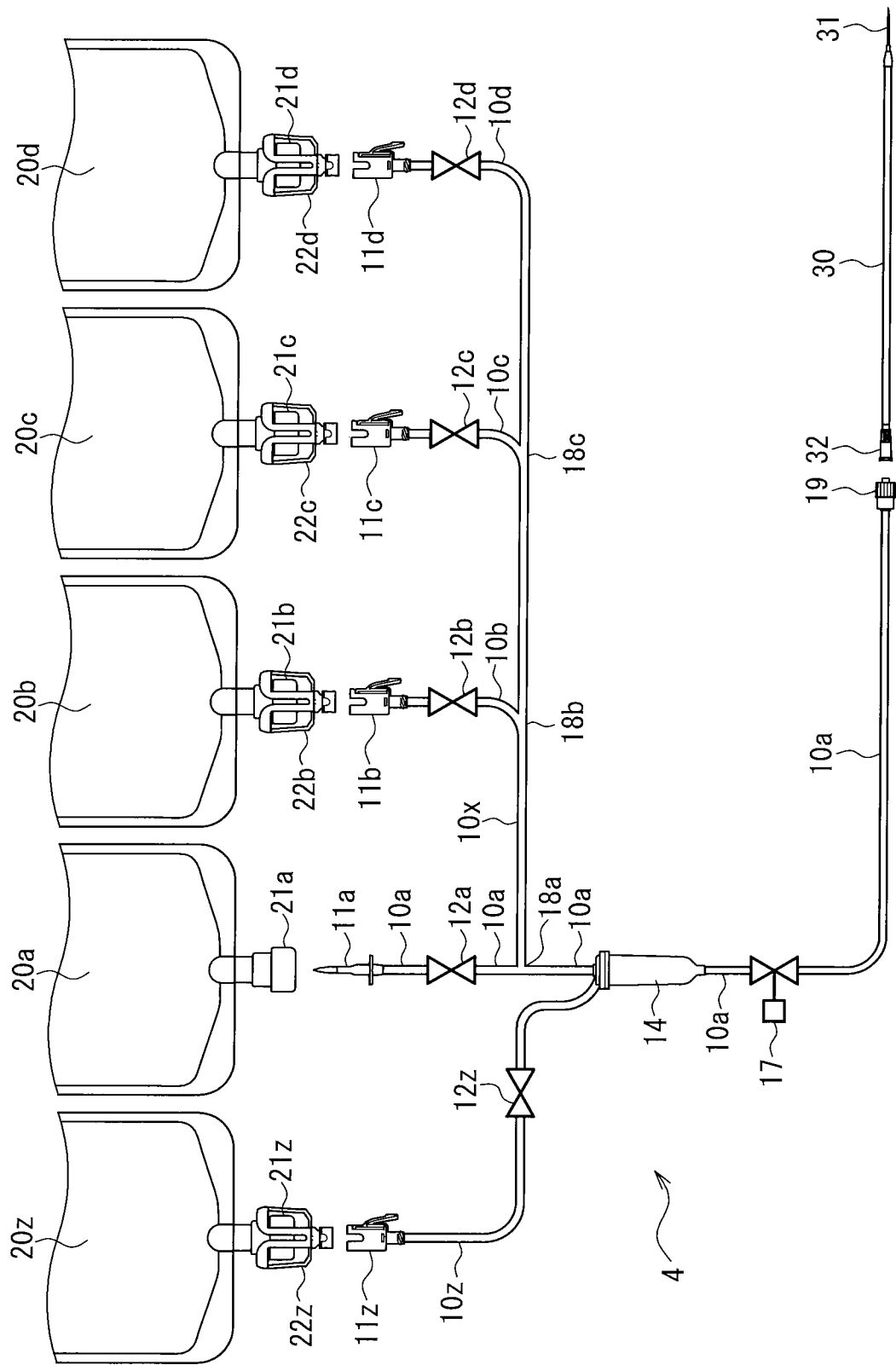
FIG. 4 shows an infusion set according to Embodiment 4 of the present invention.

An infusion set 4 and a priming method for the infusion set 4 according to Embodiment 4 of the present invention will be described, mainly regarding differences from Embodiments 1 to 3. FIG. 4 shows a schematic configuration of the infusion set 4. Similarly to the infusion set 3 (see FIG. 3) according to Embodiment 3, the infusion set 4 includes the collection container 20z and the collection flow path 10z. However, unlike Embodiment 3, the collection flow path 10z is in communication with the gas storing portion of the drip chamber 14. The gas storing portion means a portion in which air exists above a liquid surface in the drip chamber 14. Ordinarily, the drip chamber 14 is constituted by a chamber in which a liquid is stored and that is transparent and has a cylindrical shape, and a cap for closing an opening at the upper end of the chamber. In the example in FIG. 4, the lower end of the collection flow path 10z is connected to the cap. As long as the collection flow path 10z is in communication with the gas storing portion in the drip chamber 14, the lower end of the collection flow path 10z may be connected to the chamber. The infusion set 4 is the same as the infusion set 3 according to Embodiment 3, except for the above-described configuration.

A description will be given of a priming method for the infusion set 4 according to Embodiment 4 that is configured as described above.

The first container 20a to the fourth container 20d, in which the first liquid to the fourth liquid are stored, respectively, are suspended from, for example, an irrigator stand (not shown), with the ports 21a to 21d facing downward. The adapters 22b to 22d are attached to the ports 21b to 21d.

An infusion set 4 with the first to fourth open/close valves 12a to 12d, the open/close valve 12z, and the variable valve 17 in a closed state is prepared. Also, an empty collection container 20z with the port 21z to which the adapter 22z is attached is prepared. The first connector 11a in the infusion set 4 is connected to the port 21a of the first container 20a, the second to fourth connectors 11b to 11d in the infusion set 4 are connected to the adapters 22b to 22d, respectively, and the connector 11z is connected to the adapter 22z. The first flow path 10a is suspended in a substantially vertical direction due to gravity such that the first connector 11a, the first open/close valve 12a, the drip chamber 14, and the variable valve 17 are arranged in this order from the upper side toward the lower side. The second to fourth containers 20b to 20d are arranged at positions higher than the first open/close valve 12a. The downstream connector 19 is connected to the connector 32.

Initially, the first flow path 10a is primed using the first liquid (e.g. a premedication) in the first container 20a. That is to say, the first open/close valve 12a and the variable valve 17 are opened. The first liquid in the first container 20a flows from the first connector 11a into the first flow path 10a. When the first liquid reaches the tip of the needle 31 that is provided further downstream of the downstream connector 19, the first open/close valve 12a and/or the variable valve 17 are closed once. A flow path that extends from the first container 20a to the needle 31 through the first flow path 10a and the tube 30 is filled with the first liquid.

Next, the needle 31 is inserted into a patient's vein.

Next, the first open/close valve 12a and the variable valve 17 are opened again. A drip of the first liquid is started. The flow rate of the first liquid can be checked in the drip chamber 14. The opening of the variable valve 17 is adjusted such that the flow rate of the first liquid takes a predetermined value. It is checked that the liquid surface in the drip chamber 14 is at a predetermined height (position).

Upon the first liquid in the first container 20a running out, air in the first container 20a flows out, following the first liquid, from the port 21a into the first flow path 10a. An interface (gas-liquid interface or liquid surface) between the first liquid and the air moves down in the first flow path 10a. When dripping of the first liquid in the drip chamber 14 ends, the first open/close valve 12a and the variable valve 17 are closed. The drip of the first liquid is temporarily discontinued. A portion from the gas storing portion in the drip chamber 14 to the first container 20a is filled with the air that has flowed out of the first container 20a, and a portion on the downstream side (on the downstream connector 19 side) of the liquid surface in the drip chamber 14 is filled with the first liquid.

Next, the open/close valve 12z and the second open/close valve 12b are opened. The second liquid in the second container 20b flows into the second flow path 10b. Since the variable valve 17 and the first, third, and fourth open/close valves 12a, 12c, and 12d are closed, the second liquid moves air that has been present in the second flow path 10b toward the collection container 20z through the first branching portion 18a, the first flow path 10a, the drip chamber 14, and the collection flow path 10z in this order. The second liquid flows into the drip chamber 14 through the first branching portion 18a and the first flow path 10a in this order. After checking that dripping of the second liquid has started in the drip chamber 14, the open/close valve 12z is closed, and the variable valve 17 is opened. Thereafter, the second liquid moves down the first flow path 10a, and flows toward the downstream connector 19. Thus, the drip of the first liquid remaining in the first flow path 10a is resumed, and subsequently, a drip of the second liquid is started. The flow rate of the second liquid can be checked in the drip chamber 14. The opening of the variable valve 17 is adjusted such that the flow rate of the second liquid takes a predetermined value. It is checked that the liquid surface in the drip chamber 14 is at a predetermined height (position). Air that has been present in the second flow path 10b before the second open/close valve 12b is opened is confined to the gas storing portion in the drip cylinder 14, the collection flow path 10z, and the collection container 20z.

Upon the second liquid in the second container 20b running out, air in the second container 20b flows out, following the second liquid, from the port 21b into the second flow path 10b. An interface (gas-liquid interface or liquid surface) between the second liquid and the air moves down in the second flow path 10b. When dripping of the second liquid in the drip chamber 14 ends, the second open/close valve 12b and the variable valve 17 are closed. The drip of the second liquid is temporarily discontinued. A portion from the gas storing portion in the drip chamber 14 to the second container 20b is filled with the air that has flowed out of the second container 20b, and a portion on the downstream side (on the downstream connector 19 side) of the liquid surface in the drip chamber 14 is filled with the second liquid.

Next, the open/close valve 12z and the third open/close valve 12c are opened. The third liquid in the third container 20c flows into the third flow path 10c. Since the variable valve 17 and the first, second, and fourth open/close valves 12a, 12b, and 12d are closed, the third liquid moves air that has been present in the third flow path 10c toward the collection container 20z through the first branching portion 18a, the first flow path 10a, the drip chamber 14, and the collection flow path 10z in this order. The third liquid flows into the drip chamber 14 through the first branching portion 18a and the first flow path 10a in this order. After checking that dripping of the third liquid has started in the drip chamber 14, the open/close valve 12z is closed, and the variable valve 17 is opened. Thereafter, the third liquid moves down the first flow path 10a, and flows toward the downstream connector 19. Thus, the drip of the second liquid remaining in the first flow path 10a is resumed, and subsequently, a drip of the third liquid is started. The flow rate of the third liquid can be checked in the drip chamber 14. The opening of the variable valve 17 is adjusted such that the flow rate of the third liquid takes a predetermined value. It is checked that the liquid surface in the drip chamber 14 is at a predetermined height (position). Air that has been present in the third flow path 10c before the third open/close valve 12c is opened is confined to the gas storing portion in the drip cylinder 14, the collection flow path 10z, and the collection container 20z.

Then, the fourth flow path 10d is primed using the fourth liquid in the fourth container 20d, and subsequently a drip of the fourth liquid is given, in accordance with the same procedure. After the fourth liquid in the fourth container 20d has run out, the fourth open/close valve 12d and the variable valve 17 are closed. The drips of the first liquid to the fourth liquid thus end. The needle 31 is pulled out of the patient. The infusion set 4 is discarded with the first container 20a to the fourth container 20d, the collection container 20z, and the tube 30 connected thereto.

Similarly to Embodiment 1, with the infusion set 4 according to Embodiment 4, the side-injection lines (second to fourth flow paths 10b to 10d) are primed, line-by-line, after a drip of the first liquid has started and immediately before a drip of the liquids (second liquid to fourth liquids) corresponding to the respective side-injection lines starts. Furthermore, the liquids stored in the container connected to the respective side-injection lines are used as priming solutions for the side-injection lines.

Air that has been present in the side-injection lines (second and third flow paths 10b and 10c) before being primed is confined to the infusion set 4 and the collection container 20z due to priming of these side-injection lines (second and third flow paths 10b and 10c) and does not leak out to the outside. In addition, air that has flowed out, following the liquids (second and third liquids), from the containers (second and third containers 20b and 20c) to the side-injection lines (second and third flow paths 10b and 10c) is also confined to the infusion set 4 and the collection container 20z due to priming of other side-injection lines (third and fourth flow paths 10c and 10d) that is to be performed immediately after the outflow of the air, and does not leak out to the outside. Even if a side-injection line is primed using a hazardous medical solution, the hazardous medical solution and vapor thereof do not leak out to the outside. This is advantageous for reducing the likelihood that the operator who performs priming is exposed to the medicine.

Air that has been discharged from the side-injection lines due to priming is collected into the dedicated collection container 20z, similarly to Embodiment 3. As described in Embodiment 3, in Embodiment 4 as well, the configuration of the collection container 20z and the collection line is not limited to that in FIG. 4 and may be modified in any manner.

In the above-described priming method for the infusion set 4, the first to fourth open/close valves 12a to 12d and the variable valve 17 are closed when dripping of the first to fourth liquids ends in the drip chamber 14. However, in the present invention, the time when dripping of the first to fourth liquids ends in the drip chamber 14 need not accurately coincide with the time when the valves 12a to 12d and 17 are closed. The valves 12a to 12d and 17 may be closed before dripping in the drip chamber 14 ends. Specifically, the valves 12a to 12d and 17 may be closed when an interface (gas-liquid interface) between the first to fourth liquids and the following air reaches a section (branch section) of the first flow path 10a between the first open/close valve 12a and the drip chamber 14, respectively.

Embodiment 4 is the same as Embodiments 1 to 3, except for the above-described configuration. The descriptions of Embodiments 1 to 3 also apply to Embodiment 4 as appropriate.

Embodiment 5

Figure 5:
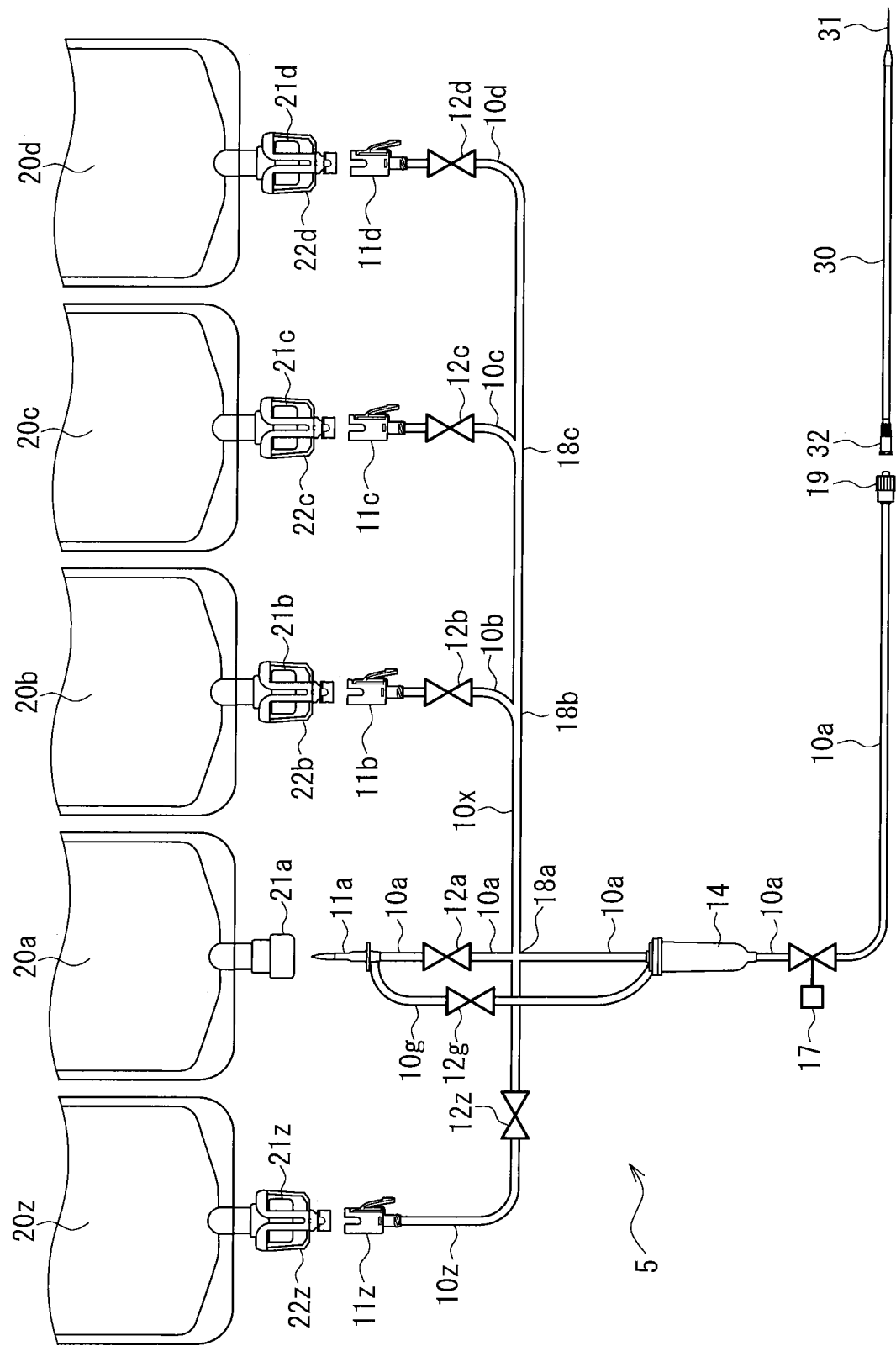
FIG. 5 shows an infusion set according to Embodiment 5 of the present invention.

An infusion set 5 and a priming method for the infusion set 5 according to Embodiment 5 of the present invention will be described, mainly regarding differences from Embodiments 1 to 4. FIG. 5 shows a schematic configuration of the infusion set 5.

Similarly to the infusion set 2 according to Embodiment 2, the infusion set 5 includes the bypass flow path 10g that brings the gas storing portion of the drip chamber 14 in communication with a portion of the first flow path 10a on the upstream side (on the first connector 11a side) of the first open/close valve 12a or the first connector 11a. The open/close valve (bypass flow path open/close valve) 12g is provided on the bypass flow path 10g.

Furthermore, the infusion set 5 includes the collection container 20z and the collection flow path 10z, similarly to the infusion set 3 according to Embodiment 3. The collection container 20z includes the port 21z. One end of the collection flow path 10z is in communication with the first branching portion 18a, and the other end is provided with a connector (collection container connector) 11z. The connector 11z is connected to the port 21z of the collection container 20z via the adapter (collection container adapter) 22z. The open/close valve (collection flow path open/close valve) 12z is provided on the collection flow path 10z.

A description will be given of a priming method for the infusion set 5 according to Embodiment 5 that is configured as described above.

The first container 20a to the fourth container 20d, in which the first liquid to the fourth liquid are stored, respectively, are suspended from, for example, an irrigator stand (not shown), with the ports 21a to 21d facing downward. The adapters 22b to 22d are attached to the ports 21b to 21d.

An infusion set 5 with the first to fourth open/close valves 12a to 12d, the open/close valve 12g, the open/close valve 12z, and the variable valve 17 in a closed state is prepared. Also, an empty collection container 20z with the port 21z to which the adapter 22z is attached is prepared. The first connector 11a in the infusion set 5 is connected to the port 21a of the first container 20a, the second to fourth connectors 11b to 11d in the infusion set 5 are connected to the adapters 22b to 22d, respectively, and the connector 11z is connected to the adapter 22z. The first flow path 10a is suspended in a substantially vertical direction due to gravity such that the first connector 11a, the first open/close valve 12a, the drip chamber 14, and the variable valve 17 are arranged in this order from the upper side toward the lower side. The second to fourth containers 20b to 20d are arranged at positions higher than the first open/close valve 12a. The downstream connector 19 is connected to the connector 32.

Initially, the first flow path 10a is primed using the first liquid (e.g. a premedication) in the first container 20a. That is to say, the first open/close valve 12a and the variable valve 17 are opened. The first liquid in the first container 20a flows from the first connector 11a into the first flow path 10a. When the first liquid reaches the tip of the needle 31 that is provided further downstream of the downstream connector 19, the first open/close valve 12a and/or the variable valve 17 are closed once. A flow path that extends from the first container 20a to the needle 31 through the first flow path 10a and the tube 30 is filled with the first liquid.

Next, the needle 31 is inserted into a patient's vein.

Next, the first open/close valve 12a and the variable valve 17 are opened again. A drip of the first liquid is started. The flow rate of the first liquid can be checked in the drip chamber 14. The opening of the variable valve 17 is adjusted such that the flow rate of the first liquid takes a predetermined value. It is checked that the liquid surface in the liquid chamber 14 is at a predetermined height (position).

Upon the first liquid in the first container 20a running out, air in the first container 20a flows out, following the first liquid, from the port 21a into the first flow path 10a. An interface (gas-liquid interface or liquid surface) between the first liquid and the air moves down in the first flow path 10a. When the dripping of the first liquid in the liquid chamber 14 ends, the first open/close valve 12a and the variable valve 17 are closed. The drip of the first liquid is temporarily discontinued. A portion from the gas storing portion in the drip chamber 14 to the first container 20a is filled with the air that has flowed out of the first container 20a, and a portion on the downstream side (on the downstream connector 19 side) of the liquid surface in the drip chamber 14 is filled with the first liquid.

Next, the open/close valve 12z and the second open/close valve 12b are opened. The second liquid in the second container 20b flows into the second flow path 10b. Since the variable valve 17, the first, third and fourth open/close valves 12a, 12c, and 12d, and the open/close valve 12g are closed, the second liquid moves air that has been present in the second flow path 10b toward the collection container 20z through the first branching portion 18a and the collection flow path 10z in this order.

When an interface (gas-liquid interface or liquid surface) between the air and the second liquid reaches the first branching portion 18a, the open/close valve 12z is closed, and the open/close valve 12g is opened. The second liquid moves down the first flow path 10a through the first branching portion 18a. Since the variable valve 17 is closed, the second liquid moves the air that has been present in a portion of the first flow path 10a from the first branching portion 18a to the drip chamber 14 toward the first container 20a through the gas storing portion of the drip chamber 14 and the bypass flow path 10g in this order. The second liquid flows into the drip chamber 14, following the air. After checking that dripping of the second liquid has started in the drip chamber 14, the open/close valve 12g is closed, and the variable valve 17 is opened. Thereafter, the second liquid moves down the first flow path 10a, and flows toward the downstream connector 19. Thus, the drip of the first liquid remaining in the first flow path 10a is resumed, and subsequently, a drip of the second liquid is started. The flow rate of the second liquid can be checked in the drip chamber 14. The opening of the variable valve 17 is adjusted such that the flow rate of the second liquid takes a predetermined value. It is checked that the liquid surface in the drip chamber 14 is at a predetermined height (position). Air that has been present in the second flow path 10b before the second open/close valve 12b is opened is confined to the collection flow path 10z, the collection container 20z, the gas storing portion in the drip chamber 14, the bypass flow path 10g, and the first container 20a.

Upon the second liquid in the second container 20b running out, air in the second container 20b flows out, following the second liquid, from the port 21b into the second flow path 10b. An interface (gas-liquid interface or liquid surface) between the second liquid and the air moves down in the second flow path 10b. When the dripping of the second liquid in the drip chamber 14 ends, the second open/close valve 12b and the variable valve 17 are closed. The drip of the second liquid is temporarily discontinued. A portion from the gas storing portion in the drip chamber 14 to the second container 20b is filled with the air that has flowed out of the second container 20b, and a portion on the downstream side (on the downstream connector 19 side) of the liquid surface in the drip chamber 14 is filled with the second liquid.

Next, the open/close valve 12z and the third open/close valve 12c are opened. The third liquid in the third container 20c flows into the third flow path 10c. Since the variable valve 17, the first, second, and fourth open/close valves 12a, 12b, and 12d, and the open/close valve 12g are closed, the third liquid moves air that has been present in the third flow path 10c toward the collection container 20z through the first branching portion 18a and the collection flow path 10z in this order.

When an interface (gas-liquid interface or liquid surface) between the air and the third liquid reaches the first branching portion 18a, the open/close valve 12z is closed, and the open/close valve 12g is opened. The third liquid moves down the first flow path 10a through the first branching portion 18a. Since the variable valve 17 is closed, the third liquid moves the air that has been present in a portion of the first flow path 10a from the first branching portion 18a to the drip chamber 14 toward the first container 20a through the gas storing portion of the drip chamber 14 and the bypass flow path 10g in this order. The third liquid flows into the drip chamber 14, following the air. After checking that dripping of the third liquid has started in the drip chamber 14, the open/close valve 12g is closed, and the variable valve 17 is opened. Thereafter, the third liquid moves down the first flow path 10a, and flows toward the downstream connector 19. Thus, the drip of the second liquid remaining in the first flow path 10a is resumed, and subsequently, a drip of the third liquid is started. The flow rate of the third liquid can be checked in the drip chamber 14. The opening of the variable valve 17 is adjusted such that the flow rate of the third liquid takes a predetermined value. It is checked that the liquid surface in the drip chamber 14 is at a predetermined height (position). Air that has been present in the third flow path 10c before the third open/close valve 12c is opened is confined to the collection flow path 10z, the collection container 20z, the gas storing portion in the drip chamber 14, the bypass flow path 10g, and the first container 20a.

Then, the fourth flow path 10d is primed using the fourth liquid in the fourth container 20d, and subsequently a drip of the fourth liquid is given, in accordance with the same procedure. After the fourth liquid in the fourth container 20d has run out, the fourth open/close valve 12d and the variable valve 17 are closed. The drips of the first liquid to the fourth liquid thus end. The needle 31 is pulled out of the patient. The infusion set 5 is discarded with the first container 20a to the fourth container 20d, the collection container 20z, and the tube 30 connected thereto.

Similarly to Embodiment 1, with the infusion set 5 according to Embodiment 5, the side-injection lines (second to fourth flow paths 10b to 10d) are primed, line-by-line, after a drip of the first liquid has started and immediately before a drip of the liquids (second liquid to fourth liquids) corresponding to the respective side-injection lines starts. Furthermore, the liquids stored in the container connected to the respective side-injection lines are used as priming solutions for the side-injection lines.

Air that has been present in the side-injection lines (second and third flow paths 10b and 10c) before being primed is confined to the infusion set 5, the collection container 20z, and the first container 20a due to priming of these side-injection lines (second and third flow paths 10b and 10c) and does not leak out to the outside. In addition, air that has flowed out, following the liquids (second and third liquids), from the containers (second and third containers 20b and 20c) to the side-injection lines (second and third flow paths 10b and 10c) is also confined to the infusion set 5, the collection container 20z, and the first container 20a due to priming of other side-injection lines (third and fourth flow paths 10c and 10d) that is to be performed immediately after the outflow of the air, and does not leak out to the outside. Even if a side-injection line is primed using a hazardous medical solution, the hazardous medical solution and vapor thereof do not leak out to the outside. This is advantageous for reducing the likelihood that the operator who performs priming is exposed to the medicine.

The configuration of the collection line that brings the collection container 20z into communication with the first branching portion 18a is not limited to that in FIG. 5, and may be modified in any manner as described in Embodiment 3.

In the above-described priming method for the infusion set 5, the first to fourth open/close valves 12a to 12d and the variable valve 17 are closed when dripping of the first to fourth liquids in the drip chamber 14 ends. However, in the present invention, the time when dripping of the first to fourth liquids in the drip chamber 14 ends need not accurately coincide with the time when the valves 12a to 12d and 17 are closed. The valves 12a to 12d and 17 may be closed before dripping in the drip chamber 14 ends, specifically when an interface (gas-liquid interface) between the first to fourth liquids and air that has been present in the first to fourth containers 20a to 20d reaches a section (branch section) between the first open/close valves 12a and the drip chamber 14, respectively.

In FIG. 5, the collection flow path 10z is connected to the first branching portion 18a, but the present invention is not limited thereto. The collection flow path 10z need only be in communication with a section (branch section) of the first flow path 10a between the first open/close valve 12a and the drip chamber 14.

Embodiment 5 is the same as Embodiments 1 to 4, except for the above-described configuration. The descriptions of Embodiments 1 to 4 also apply to Embodiment 5 as appropriate.

Embodiment 6

Figure 6:
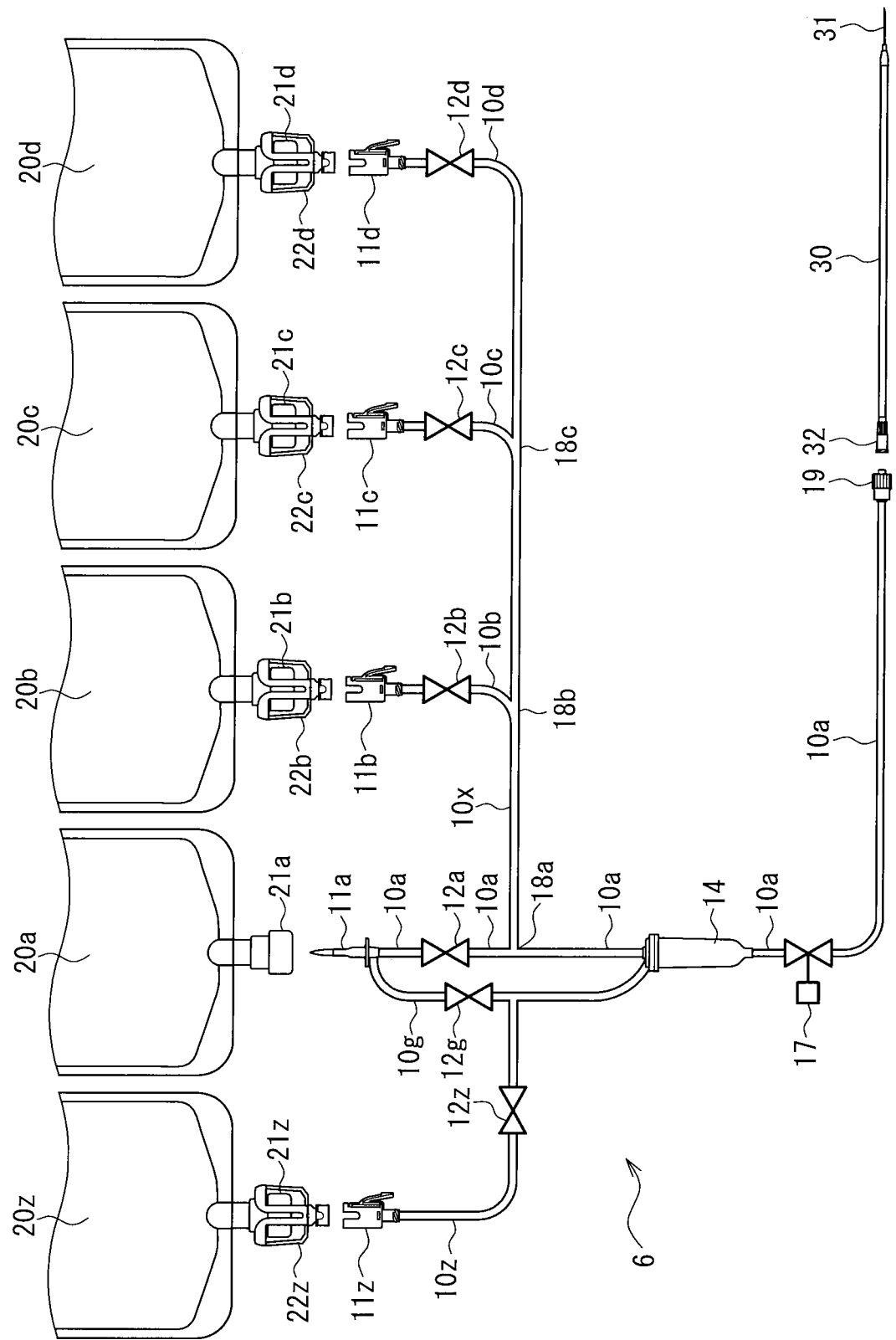
FIG. 6 shows an infusion set according to Embodiment 6 of the present invention.

An infusion set 6 and a priming method for the infusion set 6 according to Embodiment 6 of the present invention will be described, mainly regarding differences from Embodiments 1 to 5. FIG. 6 shows a schematic configuration of the infusion set 6.

Similarly to the infusion sets 2 and 5 according to Embodiments 2 and 5, the infusion set 6 includes the bypass flow path 10g that brings the gas storing portion of the drip chamber 14 in communication with a portion of the first flow path 10a on the upstream side (on the first connector 11a side) of the first open/close valve 12a or the first connector 11a. The open/close valve (bypass flow path open/close valve) 12g is provided on the bypass flow path 10g.

Furthermore, the infusion set 6 includes the collection container 20z and the collection flow path 10z, similarly to the infusion sets 3 to 5 according to Embodiments 3 to 5. However, in Embodiment 6, the collection flow path 10z branches from a portion of the bypass flow path 10g between the drip chamber 14 and the open/close valve 12g. A connector 11z (collection container connector) is provided at a terminal of the collection flow path 10z. The collection container 20z includes a port 21z. The connector 11z is connected to the port 21z of the collection container 20z via the adapter (collection container adapter) 22z. The open/close valve (collection flow path open/close valve) 12z is provided on the collection flow path 10z.

A description will be given of a priming method for the infusion set 6 according to Embodiment 6 that is configured as described above.

The first container 20a to the fourth container 20d, in which the first liquid to the fourth liquid are stored, respectively, are suspended from, for example, an irrigator stand (not shown), with the ports 21a to 21d facing downward. The adapters 22b to 22d are attached to the ports 21b to 21d.

An infusion set 6 with the first to fourth open/close valves 12a to 12d, the open/close valve 12g, the open/close valve 12z, and the variable valve 17 in a closed state is prepared. Also, an empty collection container 20z with the port 21z to which the adapter 22z is attached is prepared. The first connector 11a in the infusion set 6 is connected to the port 21a of the first container 20a, the second to fourth connectors 11b to 11d in the infusion set 6 are connected to the adapters 22b to 22d, respectively, and the connector 11z is connected to the adapter 22z. The first flow path 10a is suspended in a substantially vertical direction due to gravity such that the first connector 11a, the first open/close valve 12a, the drip chamber 14, and the variable valve 17 are arranged in this order from the upper side toward the lower side. The second to fourth containers 20b to 20d are arranged at positions higher than the first open/close valve 12a. The downstream connector 19 is connected to the connector 32.

Initially, the first flow path 10a is primed using the first liquid (e.g. a premedication) in the first container 20a. That is to say, the first open/close valve 12a and the variable valve 17 are opened. The first liquid in the first container 20a flows from the first connector 11a into the first flow path 10a. When the first liquid reaches the tip of the needle 31 that is provided further downstream of the downstream connector 19, the first open/close valve 12a and/or the variable valve 17 are closed once. A flow path that extends from the first container 20a to the needle 31 through the first flow path 10a and the tube 30 is filled with the first liquid.

Next, the needle 31 is inserted into a patient's vein.

Next, the first open/close valve 12a and the variable valve 17 are opened again. A drip of the first liquid is started. The flow rate of the first liquid can be checked in the drip chamber 14. The opening of the variable valve 17 is adjusted such that the flow rate of the first liquid takes a predetermined value. It is checked that the liquid surface in the drip chamber 14 is at a predetermined height (position).

Upon the first liquid in the first container 20a running out, air in the first container 20a flows out, following the first liquid, from the port 21a into the first flow path 10a. An interface (gas-liquid interface or liquid surface) between the first liquid and the air moves down in the first flow path 10a. When dripping of the first liquid in the drip chamber 14 ends, the first open/close valve 12a and the variable valve 17 are closed. The drip of the first liquid is temporarily discontinued. A portion from the gas storing portion in the drip chamber 14 to the first container 20a is filled with air that has flowed out of the first container 20a, and a portion on the downstream side (on the downstream connector 19 side) of the liquid surface in the drip chamber 14 is filled with the first liquid.

Next, the open/close valve 12z and the second open/close valve 12b are opened. The second liquid in the second container 20b flows into the second flow path 10b. Since the variable valve 17 and the first, third, and fourth open/close valves 12a, 12c, and 12d and the open/close valve 12g are closed, the second liquid moves air that has been present in the second flow path 10b toward the collection container 20z through the first branching portion 18a, the first flow path 10a, the drip chamber 14, the bypass flow path 10g, and the collection flow path 10z in this order. The second liquid flows into the drip chamber 14 through the first branching portion 18a and the first flow path 10a in this order. After checking that dripping of the second liquid has started in the drip chamber 14, the open/close valve 12z is closed, and the variable valve 17 is opened. Thereafter, the second liquid moves down the first flow path 10a, and flows toward the downstream connector 19. Thus, the drip of the first liquid remaining in the first flow path 10a is resumed, and subsequently, a drip of the second liquid is started. The flow rate of the second liquid can be checked in the drip chamber 14. The opening of the variable valve 17 is adjusted such that the flow rate of the second liquid takes a predetermined value. It is checked that the liquid surface in the drip chamber 14 is at a predetermined height (position). Air that has been in the second flow path 10b before the second open/close valve 12b is opened is confined to the gas storing portion in the drip chamber 14, the bypass flow path 10g, the collection flow path 10z, and the collection container 20z.

Upon the second liquid in the second container 20b running out, air in the second container 20b flows out, following the second liquid, from the port 21b into the second flow path 10b. An interface (gas-liquid interface or liquid surface) between the second liquid and the air moves down in the second flow path 10b. When dripping of the second liquid in the drip chamber 14 ends, the second open/close valve 12b and the variable valve 17 are closed. The drip of the second liquid is temporarily discontinued. A portion from the gas storing portion in the drip chamber 14 to the second container 20b is filled with air that has flowed out of the second container 20b, and a portion on the downstream side (on the downstream connector 19 side) of the liquid surface in the drip chamber 14 is filled with the second liquid.

Next, the open/close valve 12z and the third open/close valve 12c are opened. The third liquid in the third container 20c flows into the third flow path 10c. Since the variable valve 17, the first, second, and fourth open/close valves 12a, 12b, and 12d, and the open/close valve 12g are closed, the third liquid moves air that has been present in the third flow path 10c toward the collection container 20z through the first branching portion 18a, the first flow path 10a, the drip chamber 14, the bypass flow path 10g, and the collection flow path 10z in this order. The third liquid flows into the drip chamber 14 through the first branching portion 18a and the first flow path 10a in this order. After checking that dripping of the third liquid has started in the drip chamber 14, the open/close valve 12z is closed, and the variable valve 17 is opened. Thereafter, the third liquid moves down the first flow path 10a, and flows toward the downstream connector 19. Thus, the drip of the second liquid remaining in the first flow path 10a is resumed, and subsequently, a drip of the third liquid is started. The flow rate of the third liquid can be checked in the drip chamber 14. The opening of the variable valve 17 is adjusted such that the flow rate of the third liquid takes a predetermined value. It is checked that the liquid surface in the drip chamber 14 is at a predetermined height (position). Air that has been present in the third flow path 10c before the third open/close valve 12c is opened is confined to the gas storing portion of the drip chamber 14, the bypass flow path 10g, the collection flow path 10z, and the collection container 20z.

Then, the fourth flow path 10d is primed using the fourth liquid in the fourth container 20d, and subsequently a drip of the fourth liquid is given, in accordance with the same procedure. After the fourth liquid in the fourth container 20d has run out, the fourth open/close valve 12d and the variable valve 17 are closed. The drips of the first liquid to the fourth liquid thus end. The needle 31 is pulled out of the patient. The infusion set 6 is discarded with the first container 20a to the fourth container 20d, the collection container 20z, and the tube 30 connected thereto.

In the above-described priming method, air that has been present in a side-injection line before priming, and air that has flowed out of a container to the side-injection line following the liquid are collected into the collection container 20z. In this embodiment, the air can also be collected into the first container 20a. This will be described below.

When dripping of the first liquid in the drip chamber 14 ends, the first open/close valve 12a and the variable valve 17 are closed. Next, the open/close valve 12g and the second open/close valve 12b are opened (in the above priming method, the open/close valve 12z, rather than the open/close valve 12g, is opened). The second liquid in the second container 20b flows into the second flow path 10b. The second liquid moves air that has been present in the second flow path 10b toward the first container 20a through the first branching portion 18a, the first flow path 10a, the drip chamber 14, and the bypass flow path 10g in this order. The second liquid flows into the drip chamber 14 through the first branching portion 18a and the first flow path 10a in this order. After checking that dripping of the second liquid has started in the drip chamber 14, the open/close valve 12g is closed, and the variable valve 17 is opened. Thereafter, the second liquid moves down the first flow path 10a, and flows toward the downstream connector 19. Thus, the drip of the first liquid remaining in the first flow path 10a is resumed, and subsequently, a drip of the second liquid is started. Air that has been present in the second flow path 10b before the second open/close valve 12b is opened is confined to the gas storing portion in the drip chamber 14, the bypass flow path 10g, and the first container 20a. Thereafter, when dripping of the second liquid in the drip chamber 14 ends, the second open/close valve 12b and the variable valve 17 are closed.

Next, the open/close valve 12g and the third open/close valve 12c are opened (in the above priming method, the open/close valve 12z, rather than the open/close valve 12g, is opened). The third liquid in the third container 20c flows into the third flow path 10c. The third liquid moves air that has been present in the third flow path 10c toward the first container 20a through the first branching portion 18a, the first flow path 10a, the drip chamber 14, and the bypass flow path 10g in this order. The third liquid flows into the drip chamber 14 through the first branching portion 18a and the first flow path 10a in this order. After checking that dripping of the third liquid has started in the drip chamber 14, the open/close valve 12g is closed, and the variable valve 17 is opened. Thereafter, the third liquid moves down the first flow path 10a, and flows toward the downstream connector 19. Thus, the drip of the second liquid remaining in the first flow path 10a is resumed, and subsequently, a drip of the third liquid is started. Air that has been present in the third flow path 10c before the third open/close valve 12c is opened is confined to the gas storing portion in the drip chamber 14, the bypass flow path 10g, and the first container 20a. Thereafter, when dripping of the third liquid in the drip chamber 14 ends, the third open/close valve 12c and the variable valve 17 are closed.

Next, the open/close valve 12g and the fourth open/close valve 12d may be opened to prime the fourth flow path 10d using the fourth liquid, in accordance with the same procedure.

As described above, in Embodiment 6, which one of the open/close valve 12g and the open/close valve 12z to open can be optionally selected to prime a side-injection line. Air that has been present in the side-injection line before priming and air that has flowed out of a container following the liquid, to the side-injection line is pushed out toward either the collection container 20z or the first container 20a, in accordance with that selection. Which one of the collection container 20z and the first container 20a to use to collect the air can be selected for each of the side-injection lines.

Similarly to Embodiment 1, with the infusion set 6 according to Embodiment 6, the side-injection lines (second to fourth flow paths 10b to 10d) are primed, line-by-line, after a drip of the first liquid has started and immediately before a drip of the liquids (second liquid to fourth liquids) corresponding to the respective side-injection lines starts. Furthermore, the liquids stored in the container connected to the respective side-injection lines are used as priming solutions for the side-injection lines.

Air that has been present in the side-injection lines (second and third flow paths 10b and 10c) before being primed is confined to the infusion set 6 and the container 20z or 20a due to priming of these side-injection lines (second and third flow paths 10b and 10c) and does not leak out to the outside. In addition, air that has flowed out, following the liquids (second and third liquids), from the containers (second and third containers 20b and 20c) to the side-injection lines (second and third flow paths 10b and 10c) is also confined to the infusion set 6 and the container 20z or 20a due to priming of other side-injection lines (third and fourth flow paths 10c and 10d) that is to be performed immediately after the outflow of the air, and does not leak out to the outside. Even if a side-injection line is primed using a hazardous medical solution, the hazardous medical solution and vapor thereof do not leak out to the outside. This is advantageous for reducing the likelihood that the operator who performs priming is exposed to the medicine.

The configuration of the collection line that brings the collection container 20z into communication with the first branching portion 18a is not limited to that in FIG. 6, and may be modified in any manner as described in Embodiment 3.

In the above-described priming method for the infusion set 6, the first to fourth open/close valves 12a to 12d and the variable valve 17 are closed when dripping of the first to fourth liquids in the drip chamber 14 ends. However, in the present invention, the time when dripping of the first to fourth liquids in the drip chamber 14 ends need not accurately coincide with the time when the valves 12a to 12d and 17 are closed. The valves 12a to 12d and 17 may be closed before dripping in the drip chamber 14 ends, specifically when an interface (gas-liquid interface) between the first to fourth liquids and air that has been present in the first to fourth containers 20a to 20d reaches a section (branch section) between the first open/close valves 12a and the drip chamber 14.

Embodiment 6 is the same as Embodiments 1 to 5, except for the above-described configuration. The descriptions of Embodiments 1 to 5 also apply to Embodiment 6 as appropriate.

Embodiments 1 to 6 above are merely examples. The present invention is not limited to Embodiments 1 to 6 above, and can be modified as appropriate.

In Embodiments 1 to 6 above, the second flow path 10b is primed after all of the first liquid has flowed out of the first container 20a, but the present invention is not limited thereto. After the entire first flow path (main line) 10a (preferably including the tube 30) from the first connector 11a to the downstream connector 19 has been primed with the first liquid, the second flow 10b can be primed even if the first liquid still remains in the first container 20a. This can be readily done particularly in Embodiments 3 to 6 in which air that has been present in the second flow path 10b is collected into the dedicated collection container 20z. In this case, if necessary, movement of the second liquid in the second flow path 10b may be supported by, for example, lifting the second container 20b to a position higher than the first container 20a, or slightly squashing the second container 20b.

In Embodiments 1 to 6 above, the second to fourth flow paths (side-injection lines) 10b to 10d are in communication with the first flow path (main line) 10a at the shared first branching portion 18a. This configuration is advantageous for simplifying discharge of air when priming the second to fourth flow paths 10b to 10d, and for reducing mixture of different liquids. However, the present invention is not limited thereto. For example, a configuration may alternatively be employed in which the second to fourth flow paths 10b to 10d do not have a shared flow path portion, and are in communication with the first flow path 10a at different branching portions.

The number of side-injection lines included in each infusion set does not need to be three (namely, the second to fourth flow paths 10b to 10d) as in Embodiments 1 to 6 described above, and need only be at least one. The infusion set can exhibit the above-described effects of the present invention if the infusion set includes at least one side-injection line that branches from the main line (the first flow path 10a). Preferably, the number of side-injection lines is two or more.

The infusion set according to the present invention may be configured such that side-injection lines can be additionally provided as necessary. For example, in the infusion set 1 according to Embodiment 1, a branching portion similar to the branching portions 18b and 18c is provided on the fourth flow path 10d, and a female connector is provided at a terminal of a branch flow path that branches from this branching portion. A three-way stopcock is provided at this branching portion, or an open/close valve similar to the open/close valves 12b and 12c is provided on the branch flow path. An additional side-injection line may be configured to be similar to the second to fourth flow paths 10b to 10d. A connector capable of being connected to an additional container in which a liquid is stored is provided at an upstream end of the additional side-injection line. A male connector that can be attached to and detached from the aforementioned female connector is provided at a downstream end of the additional side-injection line. By connecting the additional side-injection line to the female connector, a drip of the liquid in the additional container can be given via the additional side-injection line. The additional side-injection line can be primed similarly to priming of the second to fourth flow paths 10b to 10d. The female connector for connecting the additional side-injection line is preferably a female connector that includes a self-closing valve (which may be called a septum) (e.g. see Patent Document 4). The male connector provided at the downstream end of the additional side-injection line is preferably a self-closing male connector that includes a compressible and deformable cover for covering a male member (e.g. see a later-described connector 11 in FIG. 7 and Patent Document 5). The infusion sets 2 to 6 according to Embodiments 2 to 6 may also be configured such that side-injection lines can be additionally provided.

In the infusion sets 1 to 6 according to Embodiments 1 to 6, a three-way stopcock may be provided at the branching portion 18c. For example, when the fourth container 20d is not used, the three-way stopcock at the branching portion 18c is operated to disconnect the fourth flow path 10d from the branching portion 10x. Thus, the first to third containers 20a to 20c can be sequentially primed and a drip of the liquids therein can be given with the fourth connector 11d not connected to the fourth container 20d. A three-way stopcock may also be similarly provided at the branching portion 18b.

The infusion set may further be provided with any other members. For example, a filter for filtering a liquid, a mixture injection port for mixing a medical solution or the like with a liquid, or the like may be provided in the main line and/or the side-injection lines.

A liquid may be moved in the infusion set by using a pump (e.g. an infusion pump that is commonly used in infusion), rather than using gravity. There are cases where a pump has the functionality of the variable valve 17. In such cases, the variable valve 17 can be omitted and replaced with the pump.

The configuration of the connectors connected to the containers for storing liquids or air is not limited to a puncture needle (first connector 11a) and a lever lock connector (second to fourth connectors 11b to 11d, collection container connector 11z), and may be any configuration. All of the connectors may have the same configuration, or some of the connectors may have a configuration different from the other connectors. The connector provided on the main line may be the same as connectors provided on the side-injection lines. For example, the first connector 11a may be the same lever lock connector as the second to fourth connectors 11b to 11d, and may be connected to the port 21a of the first container 20a via an adapter that is configured similarly to the adapters 22b to 22d.

Figure 7:
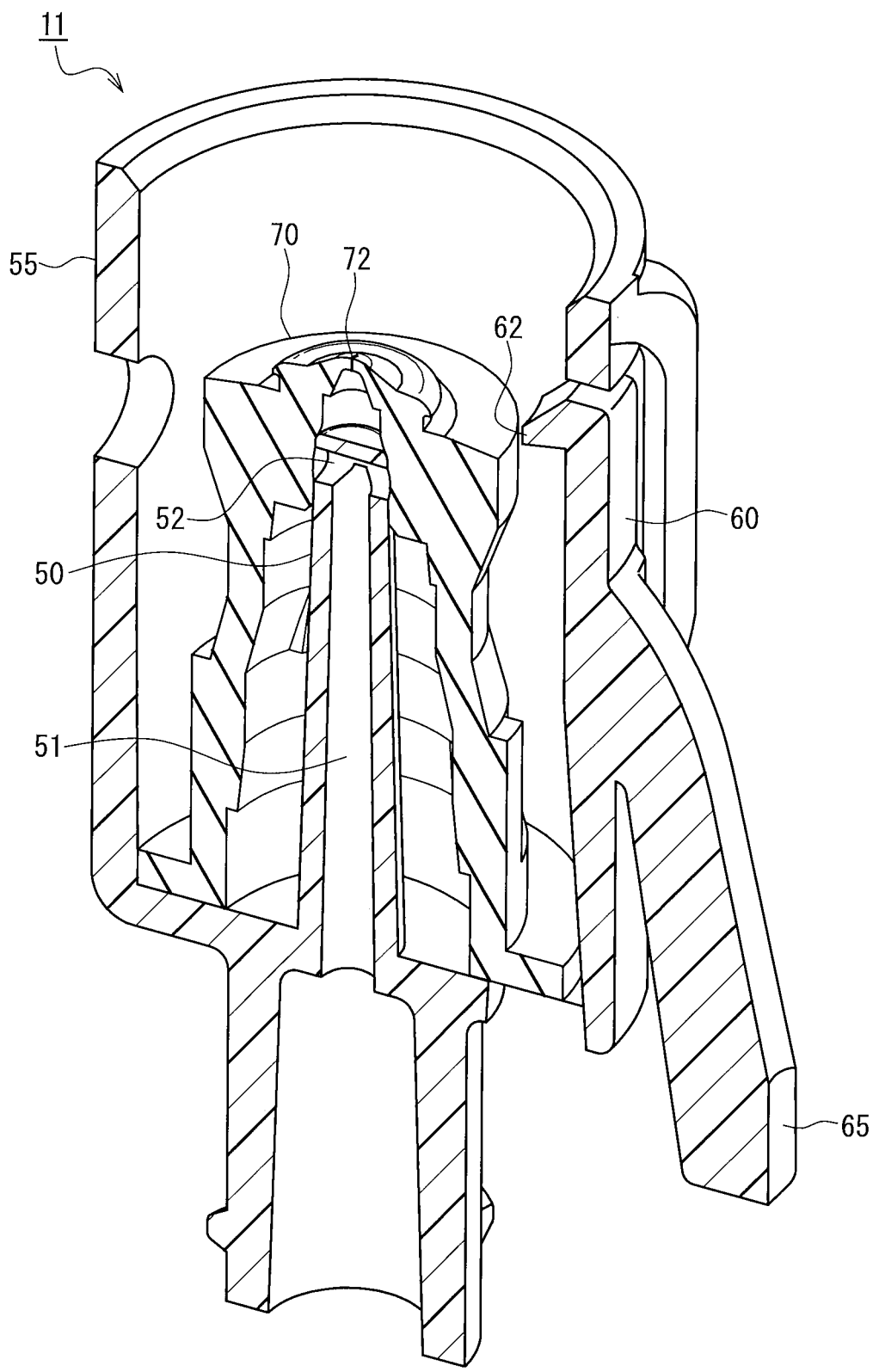
FIG. 7 is a cross-sectional perspective view showing an example of a self-closing connector that may be used in the infusion set of the present invention.

Each of the lever lock connectors may be a self-closing connector 11 such as one shown in FIG. 7. This connector 11 includes a cover 70 for covering a hole 52 provided near a leading end of a bar-shaped male member 50. The male member 50 has a flow path 51 through which a liquid flows that is formed in the longitudinal direction of the male member 50. The hole 52 is in communication with the flow path 51. A cylindrical hood 55 is disposed coaxially with the male member 50 so as to surround the male member 50. The cover 70 is made of a soft material (so-called elastomer) that has rubber elasticity (or plasticity). The material of the cover 70 is not limited, but may be, for example, isoprene rubber, silicone rubber, butyl rubber, thermoplastic elastomer, or the like. The cover 70 has, as a whole, a hollow cylindrical shape that is closed at the leading end side. A linear slit 72 with a "– (minus)" shape as viewed from above is formed at the leading end of the cover 70. Upon the connector 11 being connected to a mixture injection port of the adapter, the cover 70 is compressed and deformed in the longitudinal direction of the male member 50, and the male member 50 penetrates the slit 72 and is inserted into the mixture injection port. Upon the connector 11 being separated from the mixture injection port, the cover 70 is immediately restored to its initial shape, and the hole 52 in the male member 50 is accommodated in the cover 70. When the connector 11 is connected to the mixture injection port, the mixture injection port is inserted into the hood 55, and a claw 62, which is provided at a leading end of the lock lever 60, engages with the mixture injection port. An operation lever 65 extends from the lock lever 60. If a force that acts radially inward is applied to the operation lever 65, the claw 62 is displaced in a direction moving away from the male member 50. If a force that acts radially inward is unintentionally applied to the operation lever 65 with the connector 11 connected to the mixture injection port, there may be cases where the claw 62 is disengaged from the mixture injection port, and the connector 11 is separated from the mixture injection port. In such cases, the cover 70 immediately extends and closes the hole 52. Therefore, the liquid is less likely to leak out from the hole 52. If a connector (second and third connector 11b and 11c in Embodiments 1 to 6 above) connected to a container (second and third containers 20b and 20c in Embodiment 1 to 6 above) in which a hazardous medical solution that contains an anti-cancer agent is stored is the self-closing connector 11 shown in FIG. 7, even if the mixture injection port is unintentionally separated from the connector, the likelihood that the hazardous medical solution leaks out to the outside can be reduced. This is advantageous for preventing the operator from being exposed to the medicine during priming. In Embodiments 3 to 6, the connector 11z (see FIGS. 3 to 6) may be the self-closing connector 11 shown in FIG. 7. In this case, when the connector 11z is unintentionally separated from the mixture injection port of the adapter 22z, the likelihood that the gas in the collection flow path 10z leaks out to the outside can be reduced. This is also advantageous for preventing the operator from being exposed to the medicine during priming.

The containers for storing liquids may have any configuration. The containers may be infusion bags formed by adhering soft sheets, or may be bottles that are made of a hard material and are not substantially deformed. The ports of the containers are not limited to those sealed with rubber plugs. The configuration of the adapters that are interposed between the ports and the connectors in the infusion set is not limited to those described in the above-described embodiments either, and may also be any other configuration. The connectors may be directly connected to the ports without using the adapters.

Any type of liquid may be administered using the infusion apparatus according to the present invention. A hazardous medical solution that contains a hazardous medicine, such as an anti-cancer agent, may be administered, or a liquid that contains a nutrient, an electrolyte, or the like and poses no risk if a person is exposed thereto may be administered.

INDUSTRIAL APPLICABILITY

The method for priming an infusion set according to the present invention can be favorably used in the medical field in the case of administering a plurality of types of liquids to a patient. In particular, the infusion apparatus according to the present invention is preferable in the case of administering a hazardous medical solution, such as an anti-cancer agent, to which an operator may be exposed.

DESCRIPTION OF REFERENCE NUMERALS 1 to 6 Infusion set
10a to 10d Flow path
10g Bypass flow path
10z Collection flow path
11, 11a to 11e Connector
11z Collection container connector
12a to 12d Open/close valve
12g Bypass flow path open/close valve
12z Collection flow path open/close valve
14 Drip chamber
17 Variable valve
19 Downstream connector
20a to 20d Container
20z Collection container
50 Male member
51 Flow path in male member
52 Lateral hole in male member
60 Lock lever
70 Cover

The invention claimed is:

1. A method for priming an infusion set, the infusion set including:
- a first flow path having, at one end, a first connector, which is to be connected to a first container for storing a first liquid, and having a downstream connector at another end;
- a first open/close valve, a drip chamber, and a variable valve that are provided in this order on the first flow path from the first connector side toward the downstream connector side;
- a second flow path having, at one end, a second connector, which is to be connected to a second container for storing a second liquid, another end of the second flow path being connected to a section of the first flow path between the first open/close valve and the drip chamber; and
- a second open/close valve provided on the second flow path, the method comprising:
- a first priming step of causing the first liquid to flow from the first container into the first flow path and priming the first flow path using the first liquid; and
- a second priming step of causing the second liquid to flow from the second container into the second flow path and priming the second flow path using the second liquid,
wherein, in the second priming step, the second liquid moves air that has been present in the second flow path toward the first container; and
wherein, after the first priming step, in a state where the first liquid is being caused to flow from the first container toward the downstream connector with the second open/close valve closed and with the first open/close valve and the variable valve opened, the variable valve is closed and the second open/close valve is opened to start the second priming step.

2. The method according to claim 1, wherein the infusion set further includes:
- a third flow path having, at one end, a third connector, which is to be connected to a third container for storing a third liquid, another end of the third flow path being connected to the section of the first flow path; and
- a third open/close valve provided on the third flow path, the method further comprises a third priming step of causing the third liquid to flow from the third container into the third flow path and priming the third flow path using the third liquid, and in the third priming step, the third liquid moves air that has been present in the third flow path toward the first container.

3. The method according to claim 2, wherein, in the third priming step, the third liquid moves, toward the first container, air that has flowed out of the second container following the second liquid.

4. A method for priming an infusion set, the infusion set including:
- a first flow path having, at one end, a first connector, which is to be connected to a first container for storing a first liquid, and having a downstream connector at another end;
- a first open/close valve, a drip chamber, and a variable valve that are provided in this order on the first flow path from the first connector side toward the downstream connector side;
- a second flow path having, at one end, a second connector, which is to be connected to a second container for storing a second liquid, another end of the second flow path being connected to a section of the first flow path between the first open/close valve and the drip chamber; and
- a second open/close valve provided on the second flow path, the method comprising:
- a first priming step of causing the first liquid to flow from the first container into the first flow path and priming the first flow path using the first liquid; and
- a second priming step of causing the second liquid to flow from the second container into the second flow path and priming the second flow path using the second liquid,
wherein, in the second priming step, the second liquid moves air that has been present in the second flow path toward the first container;
wherein the infusion set further includes:
- a bypass flow path with one end in communication with a gas storing portion in the drip chamber, and another end in communication with a portion of the first flow path on the first connector side of the first open/close valve, or with the first connector; and a bypass flow path open/close valve provided on the bypass flow path, and wherein, in the second priming step, the second liquid moves air that has been present in the second flow path toward the first container through the gas storing portion in the drip chamber and the bypass flow path.

5. The method according to claim 4, wherein, after the first priming step, in a state where the first liquid is being caused to flow from the first container toward the downstream connector with the second open/close valve and the bypass flow path open/close valve closed and with the first open/close valve and the variable valve opened, the first open/close valve and the variable valve are closed and the second open/close valve and the bypass flow path open/close valve are opened to start the second priming step.

6. The method according to claim 4, wherein the infusion set further includes:

a third flow path having, at one end, a third connector, which is to be connected to a third container for storing a third liquid, another end of the third flow path being connected to the section of the first flow path; and a third open/close valve provided on the third flow path, the method further comprises a third priming step of causing the third liquid to flow from the third container into the third flow path and priming the third flow path using the third liquid, and in the third priming step, the third liquid moves air that has been present in the third flow path toward the first container through the gas storing portion in the drip chamber and the bypass flow path.

7. The method according to claim 6, wherein, in the third priming step, the third liquid moves air that has flowed out of the second container following the second liquid, toward the first container through the gas storing portion in the drip chamber and the bypass flow path.

8. A method for priming an infusion set, the infusion set including:

a first flow path having, at one end, a first connector, which is to be connected to a first container for storing a first liquid, and having a downstream connector at another end;

a first open/close valve, a drip chamber, and a variable valve that are provided in this order on the first flow path from the first connector side toward the downstream connector side;

a second flow path having, at one end, a second connector, which is to be connected to a second container for storing a second liquid, another end of the second flow path being connected to a section of the first flow path between the first open/close valve and the drip chamber;

a second open/close valve provided on the second flow path;

a collection flow path with one end connected to the section of the first flow path, the collection flow path having, at another end, a collection container connector, which is to be connected to a collection container; and a collection flow path open/close valve provided on the collection flow path, the method comprising:

a first priming step of causing the first liquid to flow from the first container into the first flow path and priming the first flow path using the first liquid; and a second priming step of causing the second liquid to flow from the second container into the second flow path and priming the second flow path using the second liquid, wherein, in the second priming step, the second liquid moves air that has been present in the second flow path toward the collection container, and wherein, after the first priming step, in a state where the first liquid is being caused to flow from the first container toward the downstream connector with the second open/close valve and the collection flow path open/close valve closed and with the first open/close valve and the variable valve opened, the first open/close valve and the variable valve are closed and the second open/close valve and the collection flow path open/close valve are opened to start the second priming step.

9. The method according to claim 8, wherein the infusion set further includes:

a third flow path having, at one end, a third connector, which is to be connected to a third container for storing a third liquid, another end of the third flow path being connected to the section of the first flow path; and a third open/close valve provided on the third flow path, the method further comprises a third priming step of causing the third liquid to flow from the third container into the third flow path and priming the third flow path using the third liquid, and in the third priming step, the third liquid moves air that has been present in the third flow path toward the collection container through the collection flow path.

10. The method according to claim 9, wherein, in the third priming step, the third liquid moves air that has flowed out of the second container following the second liquid, toward the collection container through the collection flow path.

11. A method for priming an infusion set, the infusion set including:

a first flow path having, at one end, a first connector, which is to be connected to a first container for storing a first liquid, and having a downstream connector at another end;

a first open/close valve, a drip chamber, and a variable valve that are provided in this order on the first flow path from the first connector side toward the downstream connector side;

a second flow path having, at one end, a second connector, which is to be connected to a second container for storing a second liquid, another end of the second flow path being connected to a section of the first flow path between the first open/close valve and the drip chamber;

a second open/close valve provided on the second flow path;

a collection flow path with one end in communication with a gas storing portion in the drip chamber, the collection flow path having, at another end, a collection container connector, which is to be connected to a collection container; and a collection flow path open/close valve provided on the collection flow path, the method comprising:

a first priming step of causing the first liquid to flow from the first container into the first flow path and priming the first flow path using the first liquid; and a second priming step of causing the second liquid to flow from the second container into the second flow path and priming the second flow path using the second liquid, wherein, in the second priming step, the second liquid moves air that has been present in the second flow path toward the collection container through the gas storing portion in the drip chamber and the collection flow path.

12. The method according to claim 11, wherein, after the first priming step, in a state where the first liquid is being caused to flow from the first container toward the downstream connector with the second open/close valve and the collection flow path open/close valve closed and with the first open/close valve and the variable valve opened, the first open/close valve and the variable valve are closed and the second open/close valve and the collection flow path open/close valve are opened to start the second priming step.

13. The method according to claim 11, wherein the infusion set further includes:

a third flow path having, at one end, a third connector, which is to be connected to a third container for storing a third liquid, another end of the third flow path being connected to the section of the first flow path; and a third open/close valve provided on the third flow path, the method further comprises a third priming step of causing the third liquid to flow from the third container into the third flow path and priming the third flow path using the third liquid, and in the third priming step, the third liquid moves air that has been present in the third flow path toward the collection container through the gas storing portion in the drip chamber and the collection flow path.

14. The method according to claim 13, wherein, in the third priming step, the third liquid moves air that has flowed out of the second container following the second liquid, toward the collection container through the gas storing portion in the drip chamber and the collection flow path.

15. A method for priming an infusion set, the infusion set including:

a first flow path having, at one end, a first connector, which is to be connected to a first container for storing a first liquid, and having a downstream connector at another end;

a first open/close valve, a drip chamber, and a variable valve that are provided in this order on the first flow path from the first connector side toward the downstream connector side;

a second flow path having, at one end, a second connector, which is to be connected to a second container for storing a second liquid, another end of the second flow path being connected to a section of the first flow path between the first open/close valve and the drip chamber;

a second open/close valve provided on the second flow path;

a bypass flow path with one end in communication with a gas storing portion in the drip chamber, and another end in communication with a portion of the first flow path on the first connector side of the first open/close valve, or with the first connector;

a bypass flow path open/close valve provided on the bypass flow path;

a collection flow path with one end connected to the section of the first flow path, the collection flow path having, at another end, a collection container connector, which is to be connected to a collection container; and a collection flow path open/close valve provided on the collection flow path, the method comprising:

a first priming step of causing the first liquid to flow from the first container into the first flow path and priming the first flow path using the first liquid; and a second priming step of causing the second liquid to flow from the second container into the second flow path and priming the second flow path using the second liquid, the second priming step including:

a first part of the second priming step of moving, using the second liquid, air that has been present in the second flow path toward the collection container through the collection flow path; and a second part of the second priming step of moving, using the second liquid, air that is present forward of the second liquid in a direction in which the second liquid flows, toward the first container through the gas storing portion in the drip chamber and the bypass flow path.

16. The method according to claim 15, wherein, after the first priming step, in a state where the first liquid is being caused to flow from the first container toward the downstream connector with the second open/close valve, the bypass flow path open/close valve, and the collection flow path open/close valve closed and with the first open/close valve and the variable valve opened, the first open/close valve and the variable valve are closed and the second open/close valve and the collection flow path open/close valve are opened to start the first part of the second priming step and cause the second liquid to flow from the second container into the second flow path, and after starting the first part of the second priming step, when the second liquid reaches the section of the first flow path, the collection flow path open/close valve is closed and the bypass flow path open/close valve is opened to start the second part of the second priming step and cause the second liquid to flow into the drip chamber.

17. The method according to claim 15, wherein the infusion set further includes:

a third flow path having, at one end, a third connector, which is to be connected to a third container for storing a third liquid, another end of the third flow path being connected to the section of the first flow path; and a third open/close valve provided on the third flow path, the method further comprises a third priming step of causing the third liquid to flow from the third container into the third flow path and priming the third flow path using the third liquid, and the third priming step includes:

a first part of the third priming step of moving, using the third liquid, air that has been present in the third flow path toward the collection container through the collection flow path; and a second part of the third priming step of moving, using the third liquid, air that is present forward of the third liquid in a direction in which the third liquid flows, toward the first container through the gas storing portion in the drip chamber and the bypass flow path.

18. The method according to claim 17, wherein, in the third priming step, the third liquid moves air that has flowed out of the second container following the second liquid, toward the collection container through the collection flow path, or toward the first container through the gas storing portion in the drip chamber and the bypass flow path.

19. A method for priming an infusion set, the infusion set including:
- a first flow path having, at one end, a first connector, which is to be connected to a first container for storing a first liquid, and having a downstream connector at another end;
- a first open/close valve, a drip chamber, and a variable valve that are provided in this order on the first flow path from the first connector side toward the downstream connector side;
- a second flow path having, at one end, a second connector, which is to be connected to a second container for storing a second liquid, another end of the second flow path being connected to a section of the first flow path between the first open/close valve and the drip chamber;
- a second open/close valve provided on the second flow path;
- a bypass flow path with one end in communication with a gas storing portion in the drip chamber, and another end in communication with a portion of the first flow path on the first connector side of the first open/close valve, or with the first connector;
- a bypass flow path open/close valve provided on the bypass flow path;
- a collection flow path with one end connected to a portion of the bypass flow path between the drip chamber and the bypass flow path open/close valve, the collection flow path having, at another end, a collection container connector, which is to be connected to a collection container; and
- a collection flow path open/close valve provided on the collection flow path, the method comprising:

a first priming step of causing the first liquid to flow from the first container into the first flow path and priming the first flow path using the first liquid; and a second priming step of causing the second liquid to flow from the second container into the second flow path and priming the second flow path using the second liquid, wherein, in the second priming step, the second liquid moves air that has been present in the second flow path toward the collection container through the gas storing portion in the drip chamber, the bypass flow path, and the collection flow path, or toward the first container through the gas storing portion in the drip chamber and the bypass flow path.

20. The method according to claim 19, wherein, after the first priming step, in a state where the first liquid is being caused to flow from the first container toward the downstream connector with the second open/close valve, the bypass flow path open/close valve, and the collection flow path open/close valve closed and with the first open/close valve and the variable valve opened, the first open/close valve and the variable valve are closed, the second open/close valve is opened, and the collection flow path open/close valve or the bypass flow path open/close valve is opened to start the second priming step.

21. The method according to claim 19, wherein the infusion set further includes:
- a third flow path having, at one end, a third connector, which is to be connected to a third container for storing a third liquid, another end of the third flow path being connected to the section of the first flow path; and
- a third open/close valve provided on the third flow path, the method further comprises a third priming step of causing the third liquid to flow from the third container into the third flow path and priming the third flow path using the third liquid, and in the third priming step, the third liquid moves air that has been present in the third flow path toward the collection container through the gas storing portion in the drip chamber, the bypass flow path, and the collection flow path, or toward the first container through the gas storing portion in the drip chamber and the bypass flow path.

22. The method according to claim 21, wherein, in the third priming step, the third liquid moves air that has flowed out of the second container following the second liquid, toward the collection container through the gas storing portion in the drip chamber, the bypass flow path, and the collection flow path, or toward the first container through the gas storing portion in the drip chamber and the bypass flow path.

23. An infusion set comprising:
- a first flow path having, at one end, a first connector, which is to be connected to a first container for storing a first liquid, and having a downstream connector at another end;
- a first open/close valve, a drip chamber, and a variable valve that are provided in this order on the first flow path from the first connector side toward the downstream connector side;
- a second flow path having, at one end, a second connector, which is to be connected to a second container for storing a second liquid, another end of the second flow path being connected to a section of the first flow path between the first open/close valve and the drip chamber;
- a second open/close valve provided on the second flow path;
- a bypass flow path with one end in communication with a gas storing portion in the drip chamber, and another end in communication with a portion of the first flow path on the first connector side of the first open/close valve, or with the first connector;
- a bypass flow path open/close valve provided on the bypass flow path;
- a collection flow path with one end connected to the section of the first flow path, the collection flow path having, at another end, a collection container connector, which is to be connected to a collection container; and
- a collection flow path open/close valve provided on the collection flow path.

24. An infusion set comprising:
- a first flow path having, at one end, a first connector, which is to be connected to a first container for storing a first liquid, and having a downstream connector at another end;

a first open/close valve, a drip chamber, and a variable valve that are provided in this order on the first flow path from the first connector side toward the downstream connector side;

a second flow path having, at one end, a second connector, which is to be connected to a second container for storing a second liquid, another end of the second flow path being connected to a section of the first flow path between the first open/close valve and the drip chamber;

a second open/close valve provided on the second flow path;

a bypass flow path with one end in communication with a gas storing portion in the drip chamber, and another end in communication with a portion of the first flow path on the first connector side of the first open/close valve, or with the first connector;

a bypass flow path open/close valve provided on the bypass flow path;

a collection flow path with one end connected to a portion of the bypass flow path between the drip chamber and the bypass flow path open/close valve, the collection flow path having, at another end, a collection container connector, which is to be connected to a collection container; and a collection flow path open/close valve provided on the collection flow path.

\* \* \* \* \*